United States Patent
Dubois et al.

(10) Patent No.: US 9,220,287 B2
(45) Date of Patent: Dec. 29, 2015

(54) LESQUERELLA SEED PRODUCTS AND METHOD AND DEVICE FOR PRODUCING SAME

(71) Applicant: ARKEMA FRANCE, Colombes (FR)

(72) Inventors: Jean-Luc Dubois, Millery (FR); Antoine Piccirilli, Poitiers (FR); Julien Magne, Roches-primaries-andille (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 14/348,491

(22) PCT Filed: Sep. 24, 2012

(86) PCT No.: PCT/FR2012/052124
§ 371 (c)(1),
(2) Date: Mar. 28, 2014

(87) PCT Pub. No.: WO2013/045799
PCT Pub. Date: Apr. 4, 2013

(65) Prior Publication Data
US 2014/0242252 A1     Aug. 28, 2014

(30) Foreign Application Priority Data

Sep. 30, 2011 (FR) ...................................... 11 58783

(51) Int. Cl.
*C11B 1/10* (2006.01)
*A23K 1/14* (2006.01)
(Continued)

(52) U.S. Cl.
CPC . *A23K 1/14* (2013.01); *A23D 9/013* (2013.01); *A23D 9/02* (2013.01); *A23K 1/146* (2013.01);
(Continued)

(58) Field of Classification Search
CPC .............. C11B 1/10; C11B 3/04; C11B 1/04; C11B 3/001; C11B 3/10; C11B 3/12; C11B 3/14; C11B 3/16; A23K 1/14; A23K 1/146; C10L 1/026; C12P 7/6445; C12Y 406/01013; C10G 2300/1011; C10G 2300/1014; C11C 1/007; C11C 3/003; A23D 9/013; A23D 9/02
See application file for complete search history.

(56) References Cited

U.S. PATENT DOCUMENTS 8,759,556 B2 * 6/2014 Piccirilli et al. ................ 554/30
2010/0266745 A1 10/2010 Hoang et al.
(Continued)

FOREIGN PATENT DOCUMENTS

WO  WO 2005/030911 A2  4/2005
WO  WO 2009/013349 A1  1/2009
(Continued)

OTHER PUBLICATIONS

Calrson et al. Journal of the American Oil Chemists' Society. vol. 70, No. 6. Jun. 1, 1993. pp. 579-582.*
(Continued)

*Primary Examiner* — Anthony Weier
(74) *Attorney, Agent, or Firm* — Buchanan Ingersoll & Roc P.E.

(57) ABSTRACT

A method for extraction from *Lesquerella* seeds having an acid value of less than 6 mg KOH/g, said method including the following steps: a seed-processing step i) that includes a single operation of flattening the seeds and at least one operation of drying the seeds; and a step ii) of placing the processed seeds into contact with a mixture of light anhydrous alcohol and co-solvent under temperature and time conditions that are sufficient for extracting a raw oil including phospholipids and gums, as well as obtaining a de-oiled cake.

26 Claims, 2 Drawing Sheets

(51) Int. Cl.

| | |
|---|---|
| *C12P 7/64* | (2006.01) |
| *C10L 1/02* | (2006.01) |
| *C11C 1/00* | (2006.01) |
| *A23D 9/013* | (2006.01) |
| *A23D 9/02* | (2006.01) |
| *C11B 1/04* | (2006.01) |
| *C11B 3/00* | (2006.01) |
| *C11B 3/04* | (2006.01) |
| *C11B 3/10* | (2006.01) |
| *C11B 3/12* | (2006.01) |
| *C11B 3/14* | (2006.01) |
| *C11B 3/16* | (2006.01) |
| *C11C 3/00* | (2006.01) |

(52) U.S. Cl.
CPC . *C10L 1/026* (2013.01); *C11B 1/04* (2013.01); *C11B 1/10* (2013.01); *C11B 3/001* (2013.01); *C11B 3/04* (2013.01); *C11B 3/10* (2013.01); *C11B 3/12* (2013.01); *C11B 3/14* (2013.01); *C11B 3/16* (2013.01); *C11C 1/007* (2013.01); *C11C 3/003* (2013.01); *C12P 7/6445* (2013.01)

(56) References Cited

U.S. PATENT DOCUMENTS

| | | |
|---|---|---|
| 2012/0077999 A1 | 3/2012 | Piccirilli et al. |
| 2012/0124895 A1 | 5/2012 | Dubois |
| 2012/0209018 A1 | 8/2012 | Piccirilli |
| 2013/0011887 A1* | 1/2013 | Dayton et al. ............ 435/131 |
| 2013/0052328 A1 | 2/2013 | Dubois et al. |

FOREIGN PATENT DOCUMENTS

| | | | |
|---|---|---|---|
| WO | WO 2010/076527 A1 | 7/2010 | |
| WO | WO 2010/084276 A1 | 7/2010 | |
| WO | WO 2010/122265 A1 | 10/2010 | |
| WO | WO 2011/048339 A1 | 4/2011 | |
| WO | WO 2011/092430 A1 | 8/2011 | |

OTHER PUBLICATIONS

Goodrum et al. Bioresource Technology. vol. 96, No. 7. May 1, 2005. pp. 851-855.*

International Search Report (PCT/ISA/210) mailed on Mar. 22, 2013, by the European Patent Office as the International Searching Authority for International Application No. PCT/FR2012/052124.

* cited by examiner

LESQUERELLA SEED PRODUCTS AND METHOD AND DEVICE FOR PRODUCING SAME

The present invention relates to a novel process that is capable of extracting and upgrading the majority of the components of *lesquerella* seed.

A subject of the present invention is more particularly a flexible process, which is capable of providing in a single device, according to the application, either *lesquerella* oil, or lesquerolic ester, but also of recovering the other products of *lesquerella* seed (referred to hereinbelow as the "coproducts") in a directly upgradable form:
- a cake freed of its antinutritional elements,
- gums, and
- phospholipids bearing a hydroxylated chain.

The present invention is especially directed toward upgrading lesquerolic esters for the manufacture of novel monomers, and novel polyamides derived from *lesquerella*, by means of the manufacture of 11-aminoundecanoic acid, the monomer used in the synthesis of polyamide-11,13-aminotridecanoic acid or dodecanedioic acid.

At the present time, no flexible process exists for upgrading all of the *lesquerella* seed.

The existing *lesquerella* oils are mainly obtained via processes of mechanical trituration of *lesquerella* seeds, by cold pressing or hot pressing. These oils are highly colored and have acidities that are often high (3 to 4 points of acid number). These oils are difficult to decolorize with activated earths or active charcoals, which limits the fields in which they may be upgraded. These reduced-quality criteria are intimately linked to the mechanical extraction process, which consists in treating the seeds by double-pressing: overheating of the seed and then of the cake are the cause of irreversible degradation of the oil, or even of the proteins. It is moreover noted that the double-pressing process leads to cakes that are still rich in oils (8% fat), which constitutes a significant loss of oil.

As regards the standard processes for extracting oils with solvent from oleaginous seeds (extraction with hexane), they do not make it possible to obtain, from *lesquerella* seeds, a sufficient oil extraction yield or a sufficient concentration of lesquerolic acid in the oil to be economically viable. Extraction processes using hydrocarbons such as hexane contribute toward the emission of volatile organic compounds (VOC) and to climatic warming, linked to the losses of solvent from the extraction installations. Moreover, these solvents are highly flammable and have low boiling points, which limits the working temperatures. Finally, hexane, which is the solvent most commonly used in oil extraction, is particularly suspected of being toxic by environmental agencies, hence the numerous studies to identify replacement solvents.

Also, the present invention is directed toward providing a process for improving the oil extraction yield, the quality of the raw oils from *lesquerella*, and toward providing an oil-depleted cake. For the purposes of the present invention, the term "oil-depleted cake" means a cake containing less than 3% oil and preferably less than 1% oil.

The present invention is preferably directed toward obtaining an oil extraction yield of at least 90% and preferably of at least 95%.

The present invention is also directed toward providing such a process in which the extraction coproducts, such as the cake, the phospholipids and the gums, are directly upgradable.

Typically, the fatty acid esters are prepared, after a step of solvent extraction of the oil from oleaginous plant seeds, by transesterification of this oil in the presence of alcohol and catalyst, leading to the production of an ester phase and a glycerol phase. This is the two-step process for producing fatty acid esters, for a biodiesel application, described in patent WO 2005/030 911 from the company Petroleo Brasileiro SA-Petrobras. The described process is only performed in batch mode (reaction in a stirred bed). The process is performed using oil-rich oleaginous plant seeds (with a triglyceride content ranging from 15% to 70% by weight) and after having shelled the seeds.

This process comprises a preliminary step of conditioning the seeds, during which the seeds are shelled and cleaned on a vibrating screen, and the cleaned seeds are then dried so as to reduce their moisture content to less than 0.5% by weight. The dried seeds are placed in a reactor with anhydrous alcohol; this heterogeneous mixture is converted into a homogeneous suspension by means of a stirrer. It is not until this moment that a basic catalyst is introduced into the reactor. This reaction mixture is then heated for 30 to 90 minutes, at a temperature of 30 to 78° C., leading to the transesterification of the triglycerides to esters with a high degree of conversion, of between 98% and 100%.

However, this process has the following drawbacks:
- production overcost linked to the use of shelling equipment;
- generation of solid byproducts of very low added value (husks);
- formation of fines responsible for clogging of the filters;
- production of a cake with poor mechanical strength and containing antinutritional elements, or even toxic elements or allergens depending on the seeds used.

This type of process cannot be transposed to *lesquerella* seeds for the following reasons.

- *Lesquerella* seeds are much smaller (diameter very much less than 1 mm) than those of many other plants, and shelling is technically unfeasible.
- The acidity of *lesquerella* oil is higher than that of other seeds, such as castor-oil plant seeds. The oil content of *lesquerella* seeds is low, i.e. lower than 30%. For comparative purposes, the oil content is more than 40% in castor seed, more than 30% in jatropha seed, and more than 42% in rape seed.
- In addition to being significantly less rich in oil than castor seeds (25% to 30% as opposed to 50%), the *lesquerella* seed is also poorer in hydroxylated fatty acid (55% lesquerolic acid as opposed to 85% ricinoleic acid in the castor oil plant). As a result of its lower content of hydroxylated fatty acids, *lesquerella* oil is markedly less extractable with an alcohol than castor oil, for example.
- The morphology of the seed complicates its conditioning for the purpose of obtaining a flake, which prevents optimal percolation of the solvent and does not allow efficient extraction with a single alcohol.
- Compared with other seeds, the *lesquerella* seed is very rich in phospholipids (weight content of greater than 1.5%), with highly emulsifying properties which hamper the extraction of the oil and complicate the subsequent refining of this oil.

The unfavorable conjunction of these parameters, in particular the very small size of the seed, its low oil content and the sparingly soluble nature of *lesquerella* oil in alcoholic medium (for example less soluble than castor oil), implies that the processes described in the prior art are not transposable to the *lesquerella* seed.

It is also known practice to manufacture directly fatty acid esters by transesterification by placing unshelled whole rape seeds in contact with an alcoholic medium in the presence of a catalyst. This is the process described in document WO 2009/013 349.

Document WO 2010/076 527 describes a process in which the trituration and transesterification reaction of the triglycerides present in castor oil are performed in one step from castor seeds, leading to the simultaneous production of a cake, glycerol and fatty acid esters, especially of ricinoleic acid. Document WO 2011/092 430 describes a reactive trituration process suited to jatropha seeds, in which a double-crushing is performed. The jatropha seeds do not impose the same constraints—they contain a smaller amount of phospholipids and gums—as *lesquerella* seeds. The process described for rape seeds in document WO 2009/013 349 is not suitable either for *lesquerella* seeds, since rape seed is free of gums and sparingly charged with phospholipids. Moreover, the very ligneous shell of rape and jatropha seeds gives the flake rigidity and mechanical strength, which is not the case for *lesquerella* seeds and poses a problem.

As for the oil extraction processes, the processes for manufacturing fatty acid esters used in the case of other seeds are not transposable to *lesquerella* seeds, for the following reasons.

The size of *lesquerella* seeds (about 10 mm for castor and jatropha, 2 mm for rape seed, and less than 1 mm for *lesquerella*) necessitates a suitable process;

the treatments used in certain processes, such as that described in document WO 2010/076 527, which are intended to eliminate the toxic compounds (ricin in the case of the castor-oil plant, curcin in the case of jatropha, etc.) and allergenic agents in the case of the castor-oil plant or jatropha, are not necessary in the case of *lesquerella* which does not contain such compounds, and even have, on the contrary, the effect of denaturing essential amino acids of the *lesquerella* cake;

extraction with a single alcohol proves to be insufficient in the case of *lesquerella* on account of the lower content of hydroxylated fatty acids than in the case of the castor-oil plant;

the large presence of gums in the case of *lesquerella* requires a specific separation. In particular, it is difficult, by transposing the existing processes to *lesquerella* seeds, to limit the coextraction of gums with the esters. The gums are then extremely difficult to separate from the esters.

One aim of the present invention is thus to provide a simple process, which has the fewest possible number of steps and which overcomes the above-mentioned drawbacks, for producing lesquerolic ester in a yield of at least 70%.

The present invention is also directed toward providing such a process for simultaneously coproducing an oil-depleted cake freed of its antinutritional elements, this being done directly from *lesquerella* seeds.

In point of fact, it is desirable to have available a process for treating *lesquerella* seeds which makes it possible to use *lesquerella* cake in animal feed. This is particularly important for the economy of countries that produce *lesquerella* oil (at the present time mainly the United States), since, although *lesquerella* oil or lesquerolic acid ester potentially has many industrial uses, *lesquerella* cakes still do not find any use on the industrial scale, especially on account of the presence of antinutritional elements that are indigestible or even hazardous to animals. Specifically, the *lesquerella* cakes obtained according to the existing processes contain many antinutritional elements (content much higher than 1% by weight relative to the weight of cake) which prevent their upgrading as feed cake. These antinutritional elements are especially:

glucosinolates, sulfur-bearing glycosyl compounds, as in the case of many other varieties of the mustard family, which are responsible for problems of appetite loss, especially in the case of cattle, and physiological disorders in monogastric animals;

an enzyme—thioglucosidase—which converts glucosinolates into thiocyanates, isothiocyanates, nitriles or even thiooxazolidones, these compounds affecting the thyroid gland of poultry, ruminants being much more tolerant.

The present invention proposes to provide a process for treating *lesquerella* seeds which limits the number of seed treatment steps, for the purpose of a continuous industrial application, directed toward producing either *lesquerella* oil or lesquerolic acid esters, and which makes it possible to produce cakes that can be upgraded as animal feed, while maintaining nutritional value in the cake and eliminating the antinutritional elements. In particular, the aim of the invention is to find the conditions of such a process that make it possible to use the same industrial device for alternatively producing raw oil or lesquerolic esters, and also to provide *lesquerella* seed coproducts to upgrade them.

The Applicant has now found a process that is capable of satisfying all these requirements, and even of manufacturing novel products:

a novel type of cake having the feature of containing at least 20% cellulose and/or starch, a raw oil having the feature of containing gums and at least 0.5% and preferably at least 1% of hydroxylated-chain phospholipids.

These coproducts (gums and phospholipids) are readily separated or extracted from the raw oil obtained according to the process and then upgraded. For example, the *lesquerella* gums are separated from this oil by simple centrifugation.

The Applicant has also found that certain very particular conditioning conditions, in particular of crushing the grain according to the process of the invention, make it possible to limit the coextraction of the *lesquerella* gums with the esters, and thus to considerably improve the yield of esters.

A subject of the present invention is thus a process for triturating *lesquerella* seeds in the presence of a mixture of light alcohol and of cosolvent, which makes it possible, depending on the addition or not of a basic catalyst to the mixture, to perform either (without adding catalyst) the extraction of *lesquerella* oil, or (with addition of catalyst) the extraction of oil and the simultaneous transesterification of triglycerides present in the *lesquerella* oil to lead to the production of fatty acid esters, especially of lesquerolic acid (14-hydroxy-cis-11-eicosenoic acid).

To this end, one subject of the invention is a process for extracting *lesquerella* seeds, said seeds having a degree of acidity of less than 6 mg KOH/g, said process comprising the following steps:

i) a step of conditioning the seeds;

ii) a step of placing the conditioned seeds in contact with an anhydrous light alcohol and a cosolvent under temperature and time conditions that are sufficient to allow the extraction of the vegetable oil and of a cake.

Advantageously, step ii) is followed by a step iii) of separation of the gums from the raw oil by centrifugation to obtain a degummed oil.

Advantageously, step iii) is followed by a step iv) of separation of the phospholipids from the degummed oil by refining the degummed oil. Preferably, the refining of the oil comprises at least one of the following steps:
demucilagination with phosphoric acid, and/or
deodorization under vacuum to entrain the free fatty acids, and/or
decolorization over decolorizing earths, which makes it possible to overcome the effect of the pigments during the thermal cracking.

According to a particular embodiment of the invention, said process comprises the following steps:
i) a step of conditioning the seeds;
ii) a step of placing the conditioned seeds in contact with an anhydrous light alcohol, a cosolvent and an alkaline catalyst under temperature and time conditions that are sufficient to allow the simultaneous extraction and transesterification of the vegetable oil and leading to the production of a mixture comprising fatty acid esters and glycerol, and of a cake.

This particular process according to the invention makes it possible to react "in planta" the mixture of alcohol-cosolvent and catalyst with the oil contained in the core of the seed. The alcohol acts both as solvent and as reagent.

DETAILED DESCRIPTION

Figure 1:
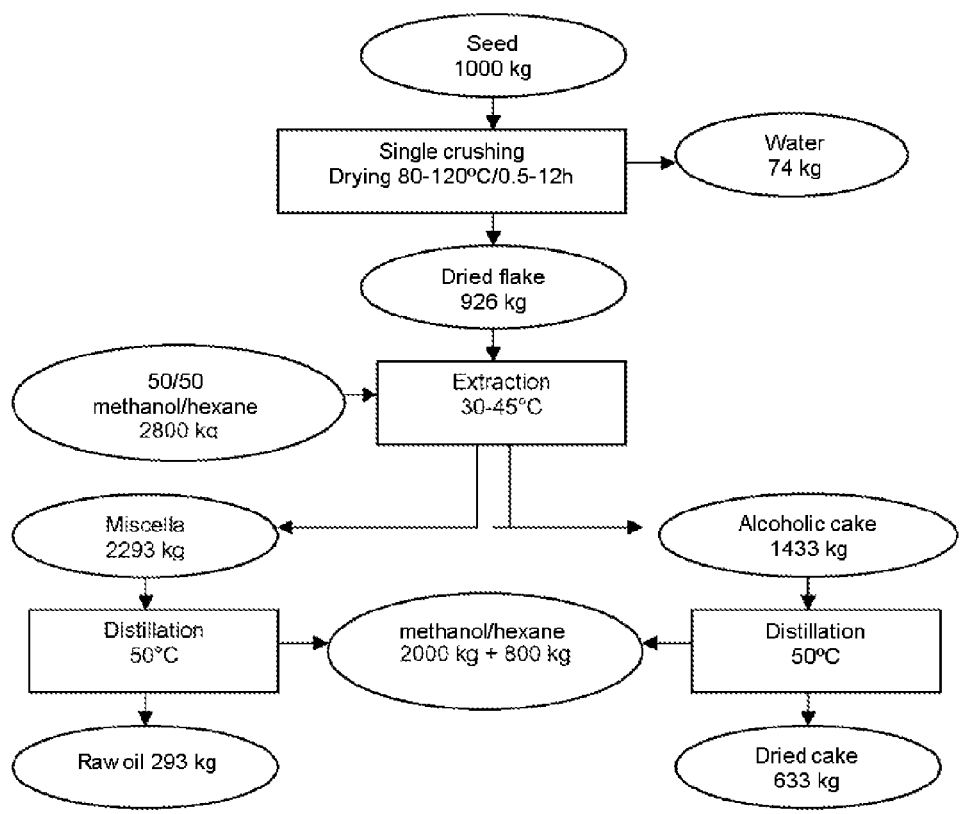
FIG. 1 depicts a process for extracting a *lesquerella* seed oil according to an embodiment of the present invention.
Figure 2:
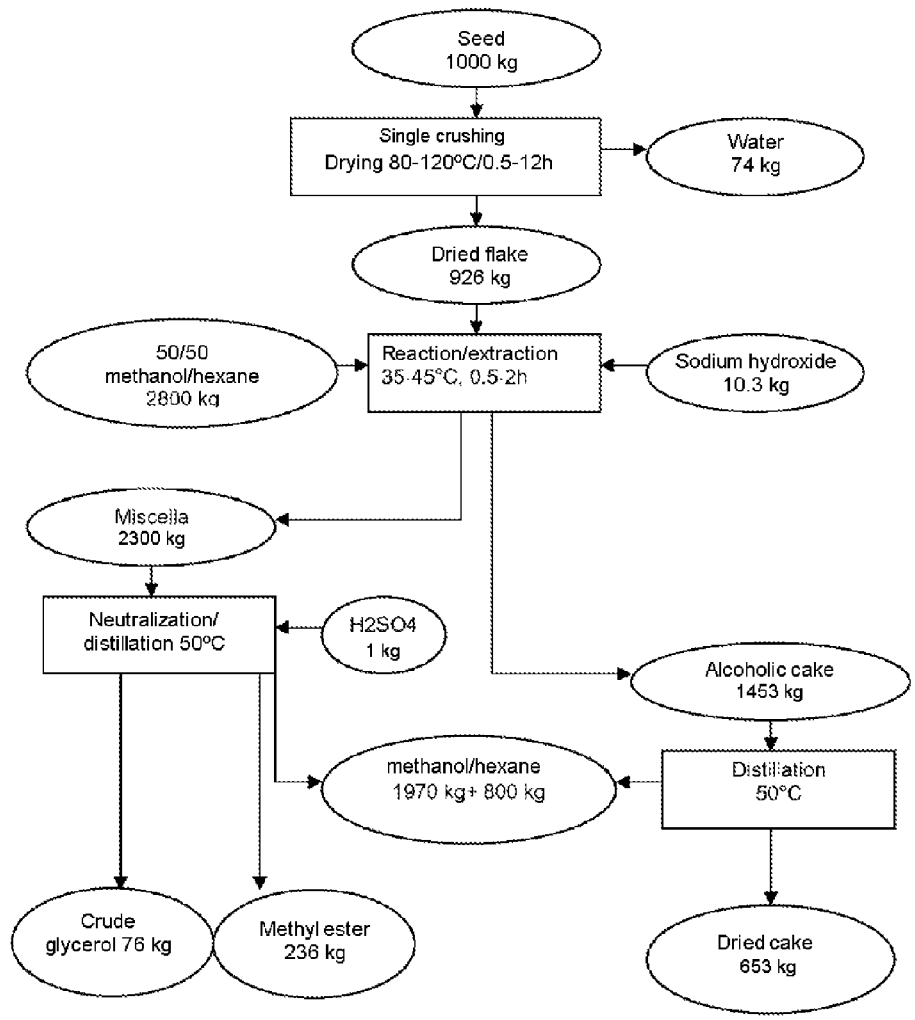
FIG. 2 depicts a process for attaining an ester from *lesquerella* seeds according to an embodiment of the present invention.

For the purposes of the present invention, the term "*lesquerella* seeds" means seeds of *lesquerella* plants, alone or as a mixture with seeds originating from at least one other oleaginous, oleo-proteaginous or proteaginous plant, including sal seeds, seeds or the mixture of seeds producing an oil containing at least 10% by weight of lesquerolic acid. It would not constitute a departure from the context of the invention if the seeds used in the process according to the invention were to originate totally or partly from genetically modified plants producing lesquerolic acid, alone or as a mixture with optionally genetically modified oleaginous plants.

Oleaginous plants are cultivated specifically for their oil-yielding seeds or fruit rich in fats, from which is extracted the oil for food, energy or industrial use. Proteaginous plants belong to the botanical group of leguminosae whose seeds are rich in proteins. Oleo-proteaginous plants are leguminosae whose seeds also contain oil.

The diameter of the *lesquerella* seeds used in the process of the invention is typically less than 1 mm. Preferably, the seeds used in the process of the invention are fresh seeds that have not undergone preheating. The harvested seeds are simply dried by the harvester to promote their storage. They may optionally undergo one or more fungicidal treatments.

Other characteristics and advantages will emerge from the detailed description of the process for treating *lesquerella* seeds according to the invention, which follows.

Step i) of Conditioning of the Seeds

The first step of the process according to the invention consists in conditioning the *lesquerella* seeds, used alone or as a mixture with other oleaginous, oleo-proteaginous or proteaginous plant seeds. This conditioning is performed on the whole, non-shelled seeds.

The object of conditioning of the seed is to make the oil as accessible as possible to the alcohol, without, however, excessively impairing its mechanical strength. This prevents the formation of a paste and of fines, which are, respectively, detrimental to the implementation of a continuous process and to the final purification of the products. Moreover, the conditioned seed should allow easy passage of the reaction fluid (alcohol-cosolvent mixture and optional basic catalyst) via simple percolation.

Characteristically, the seeds are conditioned via a sequence of operations comprising a single step of crushing and at least one step of drying them. This crushing (also known as flaking) of the *lesquerella* seeds in a single operation is preferably performed using flat rollers.

A single crushing operation is performed in the case of the invention for two reasons. Firstly, the seeds are so small that it is not necessary to perform two crushing operations. Secondly, the gums contained in the *lesquerella* seeds are polyols complexed with divalent cations. These gums are water-soluble and are extracted with alcohols. To limit the production of gums co-extracted with the esters, only one crushing operation is therefore performed.

According to one embodiment variant, the fresh seeds are crushed on a mechanical crusher with flat rollers. Preferably, the rollers used are flat because the *lesquerella* seeds are small (less than 1 mm in size), whereas ridged rollers are more suited to seeds that are much larger.

The conditioning also comprises an operation for drying the seeds thus crushed. The drying operation is performed at a temperature between 80 and 120° C., and preferably between 90 and 110° C. The crushed seeds are dried, for example in a heat-regulated ventilated oven or in a continuous hot-air band or rotary dryer. The drying time and the temperature are chosen so as to obtain a decrease in the humidity of the seeds to values of less than or equal to 2% by weight. Preferably, the drying is performed rapidly after crushing, in less than one hour, preferably after 5 to 10 minutes, at a temperature sufficient to reduce the moisture content of the seeds to 2% by weight or less. The residual moisture of the seed is determined by thermogravimetry: the seed is pre-ground, and the ground material obtained is then dried at 105° C. in a thermobalance until the weight has stabilized. The water content is expressed as a percentage of the crude material.

Step ii) of Extraction and Optionally of Simultaneous Transesterification

The seeds conditioned as described above are placed in contact with an anhydrous light alcohol and a cosolvent. Advantageously, the (alcohol-cosolvent)/seeds mass ratio is within the range from 1 to 10.

This placing in contact is performed under temperature and time conditions that are sufficient to allow the extraction of the vegetable oil and lead to the production of a mixture:
of oil (raw oil) comprising fatty acids, including lesquerolic acid, gums and phospholipids, and
of oil-freed feed cake.

Irrespective of the embodiment of the process according to the invention, the light alcohols used in step ii) is a lower aliphatic alcohol, i.e. an alcohol in which the number of carbons is within the range from 1 to 8, preferably from 1 to 5 or even better still from 1 to 4. The light alcohol is advantageously chosen from methanol, ethanol, isopropanol, n-propanol, butanol, isobutanol and 2-ethylhexanol, and mixtures thereof, and is preferably methanol.

Similarly, irrespective of the embodiment of the process according to the invention, the cosolvent used in step ii) is selected from the group: hexane, heptane, benzene, bicyclohexyl, cyclohexane, decalin, decane, essence, petroleum ether, kerosene, kerdane, gas oil, lamp oil, methylcyclohexane, naphtha (Texsolve V), Skellite, Tetradecane, Texsolve (B, C, H, S, S-2, S-66, S-LO, V), supercritical $CO_2$, pressurized propane or butane, natural solvents such as terpenes (limonene, alpha- and beta-pinene), ethers such as dimethyl ether, diethyl ether, ketones such as acetone, and mixtures of all these solvents. Preferably, the cosolvent used in the process of the invention is hexane.

Preferably, the light alcohol/cosolvent volume ratio according to the process of the invention is within the range from 0.5 to 2. Preferably, the light alcohol is methanol and the cosolvent is hexane.

Advantageously, step ii) comprises the following steps:
percolation in 3 to 9 stages of the mixture counter-currentwise relative to the seeds, at a temperature ranging from 30 to 75° C., preferably at about 40° C., for 15 to 60 minutes, and preferably 20 to 40 minutes, and then
separation and recovering of a cake and of a liquid miscella,
removal of the mixture of alcohol and cosolvent from the miscella, by evaporation of the mixture at a temperature of between 80 and 100° C. at a pressure within the range from 10 to 30 mbar.

For the present description, the recovered liquid, referred to as the "miscella", is for the purposes of the invention a suspension of oil or ester in an alcohol/cosolvent phase.

Advantageously, step ii) also comprises a step of washing the cake with the alcohol/cosolvent mixture, said washing being performed via at least three successive washes at a temperature within the range from 30 to 50° C.

According to a particular embodiment of the process, step ii) comprises a step of neutralizing the miscella with a strong acid, such as sulfuric acid, the acid content representing from 0.1% to 1% relative to the solids content of the miscella before neutralization.

The "unreactive" (or "oil route") embodiment of the process according to the invention is preferred if it is desired to upgrade the *lesquerella* gums and phospholipids, in addition to the oil and the oil-freed feed cake.

Thus, according to the process of the invention, lesquerolic acid represents from 50% to 60% by weight of the raw oil obtained.

For their part, the gums represent from 0.5% to 3% by weight of the raw oil. The *lesquerella* gums obtained according to the process of the invention are partially liposoluble and have a degree of acidity of greater than 5 mg KOH/g.

The *lesquerella* gums may advantageously be upgraded as novel gelling agents in food, cosmetic or pharmaceutical preparations. They may constitute, on the one hand, alternatives to xanthan gums obtained via biotechnology and, on the other hand, have rheological properties complementary to the gums currently on the market (guar gum, locust bean gum, etc.).

The raw oil obtained according to the process of the invention comprises at least 0.5% of hydroxylated phospholipids, i.e. phospholipids comprising hydroxyl groups, and thus comprise at least one hydroxylated chain.

The *lesquerella* phospholipids have the advantage of being derived from plant sources that are not genetically modified and may thus be advantageous substitutes for soybean lecithins. Moreover, their hydroxylated nature affords novel emulsifying properties.

Advantageously, the oil-freed *lesquerella* cake according to the invention results directly from the implementation of the process according to the invention, its use in animal feed not requiring any additional steps and/or reagents.

Advantageously, the cake derived from the process of the invention contains less than 1% by weight of oil relative to the weight of the cake.

According to the invention, the term "*lesquerella* feed cake" means a *lesquerella* cake with a total content of antinutritional elements of less than 1% by weight relative to the weight of the cake. The *lesquerella* cake may be used directly in animal feed.

The oil-freed *lesquerella* cake obtained according to the invention also has the feature of being rich in fiber, and it has a cellulose and/or starch content of greater than 20% by weight.

According to another embodiment of the invention, the *lesquerella* seed is converted directly into lesquerolic acid ester (methyl or ethyl ester) via an adaptation of a reactive variant (simple addition of basic catalyst) of the process according to the invention. In this case, the seeds conditioned as described above are placed in contact with an anhydrous light alcohol, a cosolvent and an alkaline catalyst under temperature and time conditions that are sufficient to allow the extraction and transesterification of the vegetable oil and leading to the production of a mixture comprising fatty acid esters and glycerol and of an oil-freed feed cake rich in gums and cellulose.

When it is used in the process of the invention (reactive or "ester route" embodiment), the basic catalyst (the catalyst is referred to independently as an alkaline catalyst or basic catalyst in the present description) is chosen from the group: sodium hydroxide, alcoholic sodium hydroxide, solid sodium hydroxide, potassium hydroxide, alcoholic potassium hydroxide, solid potassium hydroxide, sodium or potassium methoxide, sodium or potassium ethoxide, sodium and potassium propoxide, sodium and potassium isopropoxide, and is preferably sodium hydroxide.

The reaction takes place in a fixed-bed reactor. According to a preferred embodiment, the fixed-bed reactor is a heat-regulated percolation column equipped with a grille. A pump makes it possible to feed the column with alcohol-cosolvent mixture and optional basic catalyst. The alcohol, the cosolvent and the optional catalyst are thus added simultaneously to the reactor, which is maintained at a temperature ranging from 30 to 75° C., preferably at about 40° C.

The catalyst/alcohol-cosolvent/seeds mass ratio is preferably within the range 0/1 to 10/1 for the oil route; and within the range from 0.001 to 0.1/1 to 10/1, and preferably within the range from 0.011 to 0.1/1 to 10/1 for the ester route.

The introduction is performed at the top of the bed; the reaction liquid then percolates through the bed and is recovered in a reserve located downstream, under the bed. By pumping, the liquid is sent back to the top of the bed to diffuse again through the bed. The duration of the cycle of recirculation of the alcohol/cosolvent/optional catalyst mixture is from 15 to 60 minutes, and preferably from 20 to 40 minutes. At the end of the cycle, the introduction of liquid is stopped. Some of the liquid still present in the soaked seeds is then recovered by simple draining.

Extraction and washing of the seeds is then performed. To do this, the column is fed with the mixture of anhydrous alcohol and cosolvent which diffuses again by percolation without subsequent recycling. The amount of mixture is injected for a given period (from about 4 to 10 minutes), the liquid then being drained for a time of 10 to 20 minutes.

The miscella preferably undergoes a step of neutralization (of the optional residual basic catalyst and/or of the soaps formed) by addition of acid.

An evaporation step (generally by distillation at a temperature of about 40 to 60° C.) of solvents (alcohol and cosolvent)

from the miscella leads either to the raw oil (unreactive case) or to a mixture of phases consisting of a lighter phase rich in esters and a denser phase rich in glycerol (reactive case).

The mixture of phases is subjected to a decantation step (consisting, for example, of a static decantation in one or more decanters in parallel or in series, centrifugal decantation, combination of static or centrifugal decantation), making it possible to obtain an upper phase predominantly composed of fatty esters of lesquerolic acid (+cosolvent) and a lower phase predominantly composed of glycerol and water (glycerol phase).

Alternatively, the esters and the glycerol are separated by centrifugation.

The ester yield for the process according to the invention, calculated on the basis of the mass of ester obtained relative to the theoretical expected mass of ester, is at least 70%, preferably at least 80%, preferably at least 90%, or even better still at least 98%.

The ester phase is then subjected to a sequence directed toward recovering the fatty esters of lesquerolic acid, comprising, in a known manner, a step of washing with water followed by a step of drying under vacuum. Preferably, the esters are washed until neutral according to the following steps: addition of hot water, centrifugation, and then drying under vacuum at a temperature of between 80 and 100° C., and at a pressure within the range from 10 to 30 mbar. Advantageously, the process according to the invention also comprises at least one step of liquid/liquid extraction of said esters by means of the light alcohol counter-currentwise relative to the cosolvent, leading to the production of an alcohol phase enriched in lesquerolic acid esters, and of a cosolvent phase containing the other fatty acid esters.

The process according to the invention makes it possible to recover the majority of the upgradable products derived from the *lesquerella* seeds.

According to an advantageous embodiment of the "oil route" process, the raw oil collected is subjected to an additional step of purification of the oil.

*Lesquerella* shares a high content of hydroxylated fatty acid with another plant: the castor-oil plant. *Lesquerella* oil advantageously substitutes the castor oil in numerous applications, for example in lubricants and polyurethanes, but also as a starting material for Polyamide 11 (PA11), for which Arkema is the sole producer worldwide.

The triglycerides extracted from *lesquerella* can especially replace castor oil in applications, such as the production of dehydrated oil (containing conjugated double bonds) and the production of oxidized *lesquerella* oil. By virtue of its antiirritant properties, *lesquerella* oil may be advantageously used in facial wipes. The other envisageable uses of *lesquerella* oil especially include hair tonics, antisun agents, nucleating agents, lubricants and lubricant additives.

Lesquerolic acid is mainly intended for the manufacture of dodecanedioic acid and 2-octanol via alkaline fusion, or for the manufacture of a mixture of n-heptaldehyde and tridecylenic acid by pyrolysis. The zinc salts of lesquerolic acid have antifungal properties. Hydrogenation of lesquerolic acid produces 14-hydroxyeicosanoic acid, which is a homolog of 12-hydroxystearic acid, and which may be used especially in high-performance greases, gelling agents, nucleating agents, and as a reagent for producing novel esters, amides and polymers.

According to the advantageous embodiment of the "ester route" process, the mixture of collected liquid phases is subjected to an additional neutralizing esterification step, which consists in:

adding to the pool of liquid phases an amount of strong acid, such as sulfuric acid;

heating the acidified liquid phase thus obtained, and purifying the ester phase as described above.

The ester fraction obtained from the mixture comprising fatty acid esters and glycerol is particularly suitable for the manufacture of 11-aminoundecanoic acid, a monomer used in the synthesis of polyamide-11,13-aminotridecanoic acid and dodecanedioic acid.

Advantageously, the lesquerolic acid ester obtained is intended for the preparation of 13-aminotridecanoic acid.

In one embodiment variant, the lesquerolic acid ester derived from the process according to the invention is used directly in the synthesis of 13-aminotridecanoic acid.

Advantageously, the process of the invention also comprises the following steps:

pyrolysis or cracking of the ester, especially the methyl ester of lesquerolic acid, leading to the production of heptanal and methyl tridecenoate;

hydrolysis of the methyl tridecenoate, leading to the production of tridecenoic acid;

hydrobromuration of the tridecenoic acid, leading to the production of 13-bromotridecanoic acid, and amination of the 13-bromotridecanoic acid, leading to the production of 13-aminotridecanoic acid.

When the lesquerolic acid ester is not sufficiently pure, an additional purification step may be necessary, before subjecting it to the pyrolysis reaction.

The 13-aminotridecanoic acid obtained is mainly intended for the synthesis by condensation of polyamide-13.

According to another embodiment variant, the lesquerolic acid ester obtained according to the process of the invention is intended for the preparation of 11-aminoundecanoic acid. Advantageously, the process of the invention also comprises the following sequence of reactions:

conversion of lesquerolic acid or lesquerolic acid ester into nitrile, by reaction with ammonia, the reaction especially being catalyzed with zinc oxide;

oxidizing cleavage of the fatty nitrile obtained with ozone or aqueous hydrogen peroxide solution;

separation of the fatty acids obtained and of the nitrile-acid (10-cyanodecanoic acid) obtained;

hydrogenation of the nitrile-acid to an amino acid (11-aminoundecanoic acid).

When the lesquerolic acid ester is not sufficiently pure, an additional purification step may be necessary, before subjecting it to the nitrilation reaction.

The 11-aminoundecanoic acid thus obtained is intended mainly for the synthesis by condensation of polyamide-11.

According to yet another embodiment variant, the lesquerolic acid ester obtained according to the process of the invention is intended for the preparation of dodecanedioic acid. Advantageously, the process of the invention also comprises the following sequence of reactions:

conversion of lesquerolic acid or the lesquerolic acid ester into the sodium salt;

cleavage by pyrolysis in alkaline medium of the basic salt of lesquerolic acid;

separation of the salt of dodecanedioic acid and of 2-octanol/2-octanone coproduced, especially by evaporating off the 2-octanol/2-octanone;

acidification, especially in two steps, and crystallization of the dodecanedioic acid.

When the lesquerolic acid ester is not sufficiently pure, an additional purification step may be necessary before subjecting it to the nitrilation reaction.

The diacid thus obtained is intended mainly for the synthesis by condensation of copolyamides comprising X.12 units or monomers, in which X represents a diamine and "12" represents dodecanedioic acid, or alternatively the synthesis of solvents, for example in the form of esters. It may also serve for the preparation of the corresponding C12 diamine (dodecanediamine).

The other product obtained directly from the process according to the invention is *lesquerella* cake.

According to one embodiment variant, the lean (oil-depleted) cake soaked with alcohol is dried in a ventilated oven for 4 hours at a temperature of less than or equal to 200° C., preferably less than or equal to 150° C. and even more preferentially less than or equal to 120° C. This drying step makes it possible to remove more quickly from the cake the possible remaining solvent (alcohol and cosolvent) used during the extraction, and then to use said cake in animal feed.

The process according to the invention may without difficulty be performed continuously on the industrial scale, for example by using: a mobile-band reactor-extractor functioning continuously (such as a De Smet extractor); a rotary filter or a centrifuge. Preferably, the trituration (reactive or unreactive) is performed with the alcohol and the cosolvent (and the optional catalyst) counter-currentwise relative to the cake, over several consecutive stages.

By means of the step of specific conditioning of the *lesquerella* seeds according to the invention, it is possible to increase the contact surface area for better percolation of the alcohol-cosolvent (-catalyst) mixture and thus better extraction of the lipids, and all the more so also their consecutive conversion into esters. No preheating or preliminary impregnation of the conditioned seeds is necessary.

Starting with whole fresh seeds makes it possible:
firstly, to greatly limit the formation of fines, by making the subsequent filtration steps easier, and by limiting the allergic risk since dry fines have a tendency to become dissipated/dispersed in the ambient air;
and secondly, to maintain good mechanical strength of the bed of crushed seeds (which will form the cake), this property being very advantageous if it is desired to perform the reaction in a continuous mode.

The cakes are obtained directly from the seeds, according to the process of the invention. These cakes are free of antinutritional elements (content of less than 1% by weight relative to the weight of the cake), they maintain their physical integrity (cohesion, mechanical strength), they have a high fiber content (greater than 20% by weight relative to the weight of the cake) and an advantageous nutrient value, which allows their use in animal feed.

Preferably, the process according to the invention uses the reactive route (with basic catalyst) so as to obtain a cake freed of the antinutritional elements (their content representing less than 0.1% by weight relative to the weight of the cake). Specifically, in the reactive trituration process according to the invention, the simultaneous action of sodium hydroxide and methanol destroys the sulfur compounds of which these antinutritional elements are composed. The cakes obtained via the process for treating *lesquerella* seeds according to the invention maintain nutritional value and may be used directly in animal feed, without any risk of constituting physiological disorders in the animals that consume them.

The process according to the invention allows the manufacture of gums whose properties are similar to xanthan gum and gum Arabic, and also the manufacture of hydroxylated-chain phospholipids from *lesquerella* seeds.

Preferably, the *lesquerella* seed is upgraded according to the process of the invention by unreactive trituration. Specifically, the unreactive route ("oil route") makes it possible to extract the oil and gums and then the phospholipids after demucilagination (degumming) of the raw oil, with production of a very well oil-freed cake.

According to the unreactive trituration process, a step of vacuum distillation of the free fatty acids (physical refining of the raw oil) advantageously leads to the production of neutralized oil and of an upgradable acidic deodistillate. The gums are recovered by centrifugation of the oil, and the phospholipids are recovered in the oil refining steps.

The reactive embodiment (ester route) of the process is less advantageous as regards the upgrading of the gums and phospholipids, since, in this case, the phospholipids are found in the glycerol and part of the gums remains in the cake, the whole with a less advantageous yield of lipids. It is then particularly difficult to separate the gums from the cake and, since the phospholipids have an emulsifying effect, it is difficult to separate them from the glycerol and these two products are thus affected.

Another advantage of the process according to the invention relative to the conventional processes lies in the small amounts of water used. The operations for the refining of the raw oil, for example, are very water-intensive. This saving in water is a major asset in the context of the development of this technology in developing countries and, to a lesser extent, in rich countries since water is tending to become an increasingly expensive commodity. It is particularly important for plants such as *lesquerella*, which have the particular feature of growing in arid zones, which are thus poor in water.

In the final analysis, the present invention provides a flexible, economic process for upgrading all of the *lesquerella* seed.

A subject of the present invention is also an industrial device for performing the process according to the invention, characterized in that it comprises:
a means for conditioning *lesquerella* seeds according to step i)
a means for placing the conditioned seeds in contact with a mixture of anhydrous light alcohol and of cosolvent according to step ii), said contact means also comprising an input of basic catalyst placed in circulation or interrupted according to the demand, respectively, for lesquerolic ester or *lesquerella* oil.

The invention and advantages thereof will be understood more clearly on reading the examples below, which are given for purely illustrative purposes.

EXAMPLES

TABLE 1

Characterization of the *lesquerella* seed

| Analyses | Methods | Units | *Lesquerella* seed |
|---|---|---|---|
| Residual moisture content | Thermobalance | % crude | 7.4 |
| Fat content | V 03-908 | % DM | 29.3 (1) |
| Phospholipid content (5) | Internal | % DM | 1.9 |
| Acid number | NF T 60-204 | mg KOH/g | 4.5 |
| Saponification number | NF ISO 3657 | mg KOH/g | 177.3 |

TABLE 1-continued

Characterization of the *lesquerella* seed

| Analyses | Methods | Units | Lesquerella seed |
|---|---|---|---|
| Ester number | — | mg KOH/g | 172.8 (2) |
| Hydroxyl number | NF T 60-213 | mg KOH/g | 103.2 |
| Fatty acid profile | CPG | Relative % | |
| Palmitic (C16:0) | (Internal) | | 1.5 |
| Palmitoleic (C16:1) | | | 0.8 |
| Stearic (C18:0) | | | 2.3 |
| Oleic (C18:1) | | | 17.6 |
| Ricinoleic (C18:1-OH) | | | 0.7 |
| Linoleic (C18:2) | | | 9.1 |
| Densipoleic (C18:2-OH) | | | 0.1 |
| Linolenic (C18:3) and Arachidic (C20:0) | | | 11.6 (3) |
| Eicosenoic (C20:1) | | | 1.2 |
| Lesquerolic (C20:1-OH) | | | 52.2 |
| Auricolic (C20:2-OH) | | | 2.8 |
| Ash content | NF ISO 6884 | % DM (4) | 6.8 |
| Protein content | Kjeldahl | % DM (4) | 31.0 |
| Total starch | NFV 18-121 | % DM (4) | 3.3 |
| Cellulose | Regulation 152/2009 | % DM (4) | 14.2 |
| Amino acid profile | EC regulation N°152/2009 | Relative % | |
| Aspartic acid | | | 6.4 |
| Threonine | | | 3.7 |
| Serine | | | 4.3 |
| Glutamic acid | | | 10.7 |
| Proline | | | 5.2 |
| Glycine | | | 5.2 |
| Alanine | | | 3.9 |
| Cystine | | | 1.6 |
| Valine | | | 3.7 |
| Methionine | | | 1.2 |
| Isoleucine | | | 2.7 |
| Leucine | | | 4.9 |
| Phenylalanine | | | 3.1 |
| Histidine | | | 1.6 |
| Lysine | | | 4.9 |
| Arginine | | | 5.2 |
| Others not quantified | | | 31.7 |

(1) Calculated value; % phospholipids = % phosphorus × 26.
(2) Calculated value; $I_{ESTER} = I_{SAPO} - I_{ACID}$.
(3) The two peaks are co-eluted. Linolenic acid is predominant.
(4) Values obtained on a cake derived from the defatting of the seed with hexane.
(5) Values obtained on the oil obtained from extraction with hexane (soxhlet).

Four measurements were taken to determine the fat content (FAT) of the seed:
measurement 1: first soxhlet extraction with hexane on the fresh seed+second soxhlet extraction with hexane of the cake/result: 24.7%/DM (dry matter: DM).
measurement 2: first soxhlet extraction with hexane on the fresh seed+second soxhlet extraction with hexane of the cake/result: 29.0%/DM
measurements 3 and 4 (duplicate): first soxhlet extraction with hexane on the dried seed+second soxhlet extraction with hexane of the cake/result (mean): 29.3%
Comments:
The *lesquerella* seed is in the form of very small seeds (Ø<<1 mm), although smaller than rape seeds. In point of fact, these seeds cannot be shelled.
the fat remains relatively acidic ($I_A$=4.5).
*Lesquerella* Seeds and Cake (See Tables 1 and 1B Page 43):
it is noted that the total amount of the fractions assayed in the *lesquerella* seed is not equal to 100%. Thus, the lignin and also the soluble sugars, these fractions generally representing 10% to 20% of the cakes, were not quantified;
the whole seed has a protein content of about 28.7%.
Unreactive Trituration Tests: "Oil" Route
The unreactive trituration process was performed in the presence of three solvents or groups of solvents:
Methanol,
Methanol/Hexane (50/50),
Ethanol.
Unreactive Trituration in the Presence of Methanol
The procedure is as follows:
1. Flaking of the fresh *lesquerella* seed on a flat roller crusher.
2. The flakes are then dried for 16 hours at 100° C.
3. The flakes are placed in the percolation column.
4. Methanol is then circulated over the bed for 30 minutes at 50° C.
5. The miscella is then withdrawn and the bed of flakes is washed by five successive washes with methanol at 50° C. (5 minutes per wash).
6. The miscella is then evaporated under vacuum at 90° C. and at 20 mbar for 5 minutes.
7. The oil and the gums are separated by centrifugation. The oil yield is calculated on the basis of the mass of oil obtained versus the expected theoretical mass of oil.
8. The oil is then washed until neutral by addition of hot water and centrifugation, and is then dried under vacuum at 90° C. and 20 mbar for 5 minutes. The acid number and the composition of this oil are then measured.
9. The gums are retreated with 20% sulfuric acid and a mass of water. The mixture is heated at 90° C. for 30 minutes. After cooling, the organic phase is dissolved in hexane, washed until neutral and dried.

TABLE 2

Mass balance of the unreactive trituration process with methanol of *lesquerella* seed

| Conditions | TEST 10-E32 |
|---|---|
| Crushing tight flat rollers | Yes |
| Second crushing tight flat rollers | No |
| Drying 100° C., 16 hours | Yes |
| Flake thickness, mm | 0.16 to 0.18 |
| Catalyst content (vs flake), % | 0.0 |
| Methanol/seed mass ratio | 2 |
| Test balance | |
| Yield of solids, % (1) | 110.9 |
| Phase separation | Yes |
| Oil yield, % | 51.3 |
| Potential oil in the cake, % | 3.7 |
| (cake fat content, %) | (1.5) |
| Yield of insoluble matter in the oil extracted by centrifugation, % | 643.1 |
| Loss of oil (calculated value), % (2) | 45.0 |
| Retreatment of the insoluble matter | |
| Oil yield, % | 27.3 |
| Loss of oil (calculated value), % (2) | 17.7 |

(1) The yield of solids is the ratio times 100 of the solids obtained after evaporation of the miscella to the sum of the theoretical amounts of theoretical oil
(2) Oil loss = 100 − oil yield − potential cake oil Comments:

in the absence of catalyst, it is noted that the yield of solids is always very high (>110%), as is the yield of insoluble matter in the oil (>600%). This result clearly indicates that methanol does indeed extract non-lipid compounds;

if the cake is moderately depleted, the oil loss during the process, probably by entrainment in the gums, remains very high (45%);

the phospholipid content of the oil is 0.5% (table 3);

in qualitative terms (table 3), the oil is rather very acidic ($I_A$≈8), more acidic than the seed oil ($I_A$=4.5). By experience, on extraction of acidic oils, alcohols have a tendency to concentrate these oils;

Moreover, as a relative %, 2 points of lesquerolic acid are lost on extraction.

The retreatment with sulfuric acid of the insoluble matter (standard treatment of crude glycerol from biodiesel) leads to the recovery of 27 fat points on a potential of 45. This treatment is therefore inadequate.

TABLE 3

Analysis of the oil extracted with methanol

| Criteria | Method | Test 10-E32 Oil |
|---|---|---|
| Acid number (mg KOH/g) | EN 14104 | 7.7 |
| Fatty acid profile | EN 14105 | |
| Palmitic (C16:0) | | 1.6 |
| Palmitoleic (C16:1) | | 0.8 |
| Stearic (C18:0) | | 2.3 |
| Oleic (C18:1) | | 18.5 |
| Ricinoleic (C18:1-OH) | | 0.7 |
| Linoleic (C18:2) | | 9.9 |
| Densipoleic (18:2-OH) | | 0.2 |
| Linolenic and Arachidic | | 12.1 (1) |
| Eicosenoic (C20:1) | | 1.0 |
| Lesquerolic (C20:1-OH) | | 50.3 |
| Auricolic (20:2-OH) | | 2.6 |

TABLE 3-continued

Analysis of the oil extracted with methanol

| Criteria | Method | Test 10-E32 Oil |
|---|---|---|
| Phospholipids (%) | Internal | 0.5 (2) |
| Corrected oil yield (3), % | — | 46.6 |

(1) The two peaks are co-eluted. Linolenic acid is predominant.
(2) Calculated value; % phospholipids = % phosphorus × 26.
(3) Corrected yield = yield of extraction oil (table 1) − % phospholipids Unreactive Trituration in the Presence of a Methanol/Hexane Cosolvent The procedure is as follows:

1. Flaking of the fresh *lesquerella* seed on a flat roller crusher.
2. The flakes are then dried for 16 hours at 100° C.
3. The flakes are placed in the percolation column.
4. The methanol/hexane mixture (50/50, m/m) is then circulated on the bed for 30 minutes at 40° C.
5. The miscella is then withdrawn and the bed of flakes is washed by five successive washes with the methanol/hexane mixture at 40° C. (5 minutes per wash).
6. The miscella is then evaporated under vacuum at 90° C. and at 20 mbar for 5 minutes.
7. The oil and the gums are separated by centrifugation. The oil yield is calculated on the basis of the mass of oil obtained versus the expected theoretical mass of oil.
8. The oil is then washed until neutral by adding hot water and centrifugation, and is then dried under vacuum at 90° C. and 20 mbar for 5 minutes. The acid number and the composition of this oil are then measured.

TABLE 4

Mass balance for the process of unreactive trituration of *lesquerella* seed in the presence of a methanol/hexane mixture

| Conditions | TEST 10-E47 |
|---|---|
| Crushing tight flat rollers | Yes |
| Second crushing tight flat rollers | No |
| Drying 100° C., 16 hours | Yes |
| Flake thickness, mm | 0.16 to 0.18 |
| Catalyst content (vs flake), % | 0.0 |
| Solvents/seed mass ratio | 2 |
| Test balance | |
| Yield of solids, % (1) | 107.8 |
| Phase separation | No |
| Oil yield, % | 107.8 |
| Potential oil in the cake, % | 2.4 |
| (cake fat content, %) | (0.9) |
| Yield of insoluble matter in the oil extracted by centrifugation, % | 0.0 |
| Loss of oil (calculated value), % (2) | −10.2 |

(1) The yield of solids is the ratio times 100 of the solids obtained after evaporation of the miscella to the sum of the theoretical amounts of theoretical oil
(2) Oil loss = 100 − oil yield − potential cake oil Comments:

In the presence of a methanol/hexane mixture, the extraction yield is of the same order as previously (≈108%), whereas the extraction temperature was brought to 40° C. in order to avoid boiling of the hexane;

The content of insoluble matter is zero, which appears to indicate that if extraction of gums has taken place, these gums are partially liposoluble (<10% in the oil);

the cake remains relatively well depleted (0.9%);

the phospholipid content of the oil is 1.3% (table 5);

in qualitative terms, the extracted oil is very acidic ($I_A>11$). It is highly probable that the solubilized gums have significant acidity. Moreover, the expected lesquerolic acid content is found (52%).

TABLE 5

Analysis of the oil extracted with a methanol/hexane mixture

| Criteria | Method | Test 10-E47 oil |
| --- | --- | --- |
| Acid number (mg KOH/g) | EN 14104 | 11.2 |
| Fatty acid profile | EN 14105 | |
| Palmitic (C16:0) | | 1.6 |
| Palmitoleic (C16:1) | | 0.9 |
| Stearic (C18:0) | | 2.3 |
| Oleic (C18:1) | | 18.8 |
| Ricinoleic (C18:1-OH) | | 0.5 |
| Linoleic (C18:2) | | 10.1 |
| Densipoleic (18:2-OH) | | 0.2 |
| Linolenic and Arachidic | | 11.6 (1) |
| Eicosenoic (C20:1) | | 0.9 |
| Lesquerolic (C20:1-OH) | | 52.1 |
| Auricolic (20:2-OH) | | 2.6 |
| Phospholipids (%) | Internal | 1.3 (2) |
| Corrected oil yield (3), % | — | 106.5 |

(1) The two peaks are co-eluted. Linolenic acid is predominant.
(2) Calculated value; % phospholipids = % phosphorus × 26.
(3) Corrected yield = yield of extraction oil (table 1) − % phospholipids Unreactive Trituration in the Presence of Ethanol The test was performed under the following conditions:

1. Flaking of the fresh *lesquerella* seed on a flat roller crusher.
2. The flakes are then dried for 16 hours at 100° C.
3. The flakes are placed in the percolation column.
4. The ethanol is then circulated on the bed for 30 minutes at 50° C.
5. The miscella is then withdrawn and the bed of flakes is washed by five successive washes with ethanol at 50° C. (5 minutes per wash).
6. The miscella is then evaporated under vacuum at 90° C. and at 20 mbar for 5 minutes.
7. The oil and the gums are separated by centrifugation. The oil yield is calculated on the basis of the mass of oil obtained versus the expected theoretical mass of oil.
8. The oil is then washed until neutral by adding hot water and centrifugation, and is then dried under vacuum at 90° C. and 20 mbar for 5 minutes. The acid number and the composition of this oil are then measured.

TABLE 6

Mass balance of the process for the unreactive trituration with ethanol of *lesquerella* seed

| Conditions | TEST 10-E56 |
| --- | --- |
| Crushing tight flat rollers | Yes |
| Second crushing tight flat rollers | No |
| Drying 100° C., 16 hours | Yes |
| Flake thickness, mm | 0.16 to 0.18 |
| Catalyst content (vs flake), % | 0.0 |
| Ethanol/seed mass ratio | 2 |
| Test balance | |
| Yield of solids, % (1) | 92.0 |
| Phase separation | Yes |
| Oil yield, % | 60.9 |
| Potential oil in the cake, % (cake fat content, %) | 4.9 (2.0) |
| Yield of insoluble matter in the oil extracted by centrifugation, % | 11.2 |
| Loss of oil (calculated value), % (2) | 34.2 |

(1) The yield of solids is the ratio times 100 of the solids obtained after evaporation of the miscella to the sum of the theoretical amounts of theoretical oil
(2) Oil loss = 100 − oil yield − potential cake oil Comments:

In the presence of ethanol, the extraction yield (92%) is significantly lower than in the presence of methanol or of the methanol-hexane mixture;

the cake remains relatively well depleted;

the content of insoluble matter is about 11% with a substantial loss of oil (by entrainment in the gums, of 34%);

the phospholipid content is 1.3% (table 7). In point of fact, the corrected oil yield taking into account the phospholipid content is 59.6% (table 7).

In qualitative terms, the extracted oil is very acidic ($I_A>13$). In this case also, it is highly probable that the solubilized gums have significant acidity. Moreover, the expected lesquerolic acid content is found (53%).

TABLE 7

Analysis of the oil extracted with ethanol

| Criteria | Method | Test 10-E56 Oil |
| --- | --- | --- |
| Acid number (mg KOH/g) | EN 14104 | 13.0 |
| Fatty acid profile | EN 14105 | |
| Palmitic (C16:0) | | 1.6 |
| Palmitoleic (C16:1) | | 0.8 |
| Stearic (C18:0) | | 2.3 |
| Oleic (C18:1) | | 18.3 |
| Ricinoleic (C18:1-OH) | | 0.7 |
| Linoleic (C18:2) | | 9.6 |
| Densipoleic (18:2-OH) | | 0.3 |
| Linolenic and Arachidic | | 11.4 (1) |
| Eicosenoic (C20:1) | | 0.9 |
| Lesquerolic (C20:1-OH) | | 53.1 |
| Auricolic (20:2-OH) | | 2.5 |
| Phospholipids (%) | Internal | 0.6 (2) |

(1) The two peaks are co-eluted. Linolenic acid is predominant.
(2) Calculated value; % phospholipids = % phosphorus × 26.

Conclusion of the Unreactive Trituration Tests (Process without Catalyst)

In conclusion for these tests:

the hexane-methanol cosolvent process proves to be superior to the monosolvent (methanol, ethanol) processes with regard to the oil yield obtained;

the cake derived from this process is relatively well depleted of oil: 0.9% residual fat. This value is moreover entirely optimizable at the industrial level.

the raw oil obtained proves to be more acidic ($I_A \approx 11$) than the oil from the starting seed ($I_A=4.5$) and moreover relatively charged with phospholipids, 0.6%.

It is therefore preferable, for any industrial application, to refine the oil on the basis of a physical and chemical mixed refining, for example according to the following sequence: demucilagination with phosphoric acid, deodorization under vacuum (entrainment of the free fatty acids) and decolorization over decolorizing earths in order to overcome the pigment effect during the thermal cracking.

Reactive Trituration Tests (in the Presence of Basic Catalyst)
Reactive Trituration in the Presence of Methanol Alone, without Cosolvent (Comparative Examples)

1—Influence of the Number of Crushing Operations a—Double Crushing

The fixed-bed reaction is performed under the following conditions:

1. Flaking of the fresh *lesquerella* seed on a flat roller crusher. The flaked seed is subjected to two passes in the crusher.
2. The flakes are then dried for 16 hours at 100° C.
3. The flakes are placed in the percolation column.
4. The methanolic sodium hydroxide solution is then circulated on the bed for 30 minutes at 50° C.
5. The miscella is then withdrawn and the bed of flakes is washed by five successive washes with methanol at 50° C. (5 minutes per wash).
6. The miscella is then evaporated under vacuum at 90° C. and 20 mbar for 5 minutes.
7. The ester and the glycerol are separated by centrifugation. The ester yield is calculated on the basis of the mass of ester obtained versus the expected theoretical mass of ester.
8. The ester is then washed until neutral by adding hot water and centrifugation, and is then dried under vacuum at 90° C. and 20 mbar for 5 minutes. The acid number and the composition of this ester are then measured.

TABLE 8

Mass balance of the process for the reactive trituration of double-crushed *lesquerella* seed

| | TEST 10-E28 |
|---|---|
| Crushing tight flat rollers | Yes |
| Second crushing tight flat rollers | Yes |
| Drying 100° C., 16 hours | Yes |
| Flake thickness, mm | 0.10 to 0.15 |
| Catalyst content (vs flake), % | 0.8 |
| Methanol/seed mass ratio | 2 |
| Test balance | |
| Yield of solids, % (1) | 123.1 |
| Ester/glycerol phase separation | No |
| Yield of methyl esters, % | N.d. |
| Ester potential in the cake, % | 1.3 |
| Fat content in the cake, % DM | 0.5 |
| Glycerol yield, % | N.d. |
| Loss of esters (calculated value), % (2) | N.d. |

(1) The yield of solids is the ratio times 100 of the solids obtained after evaporation of the miscella to the sum of the theoretical amounts of ester and glycerol
(2) Loss of ester = 100 − ester yield − cake ester potential Comments:

it should be noted that after double crushing, the flake appears in the form of very fine and very compact leaflets (in principle with a large exchange surface area).

in the light of the results of table 2, it appears that under the test conditions, the flake is very well depleted, but the mixture does not undergo phase separation. In addition, given the very high value of solids (123%), it would appear that a fraction other than the lipid fraction is entrained in the medium. Thus, we strongly suspect the presence of natural gums with the characteristic gelling properties of *lesquerella*. These gums may be present to a proportion of 10% in the seed. From a chemical viewpoint, these gums are polyols complexed with divalent cations (Ca, Mg) and are extractible with water. Consequently, these gums are very certainly partly soluble in methanol. Thus, in order to limit the extraction of these gums, a single crushing operation is preferable.

b—Single Crushing

The test was performed under the following conditions:

1. Flaking of the fresh *lesquerella* seed on a flat roller crusher.
2. The flakes are then dried for 16 hours at 100° C.
3. The flakes are placed in the percolation column.
4. The methanolic sodium hydroxide solution is then circulated on the bed for 30 minutes at 50° C.
5. The miscella is then withdrawn and the bed of flakes is washed by five successive washes with methanol at 50° C. (5 minutes per wash).
6. The miscella is then evaporated under vacuum at 90° C. and at 20 mbar for 5 minutes.
7. The ester and the glycerol are separated by centrifugation. The ester yield is calculated on the basis of the mass of ester obtained versus the expected theoretical mass of ester.
8. The ester is then washed until neutral by adding hot water and centrifugation, and is then dried under vacuum at 90° C. and 20 mbar for 5 minutes. The acid number and the composition of this ester are then measured.

TABLE 9

Mass balance of the process for the reactive trituration of single-crushed *lesquerella* seed

| | TEST 10-E29 |
|---|---|
| Crushing tight flat rollers | Yes |
| Second crushing tight flat rollers | No |
| Drying 100° C., 16 hours | Yes |
| Flake thickness, mm | 0.16 to 0.18 |
| Catalyst content (vs flake), % | 0.6 |
| Methanol/seed mass ratio | 2 |
| Test balance | |
| Yield of solids, % (1) | 107.9 |
| Ester/glycerol phase separation | Yes |
| Yield of methyl esters, % | 83.7 (3) |
| Ester potential in the cake, % | 2.3 |
| Fat content in the cake, % DM | 1.1 |
| Glycerol yield, % | 469.3 |
| Loss of esters (calculated value), % (2) | 14.0 |

(1) The yield of solids is the ratio times 100 of the solids obtained after evaporation of the miscella to the sum of the theoretical amounts of ester and glycerol
(2) Loss of ester = 100 − ester yield − cake ester potential
(3) Ester not washed since strong emulsion.

Comments:

it should be noted that the ester obtained could not be washed. In the presence of water, a very stable emulsion is formed. The yield of 83.7% appears to be highly overestimated since the ester is probably polluted with emulsifying molecules (glycerides or gums).

similarly, the glycerol yield literally exploded (soaps, gums, soluble sugars, etc.).

It should be noted that under these conditions, the cake remains correctly depleted.

2—Influence of the Amount of Catalyst

For the following tests, the single-crushed seed is used.

TABLE 10

Mass balance of the process for the reactive trituration of *lesquerella* seed/effect of the amount of catalyst

|  | TEST 10-E29 | TEST 10-E31 | TEST 10-E30 |
|---|---|---|---|
| Crushing tight flat rollers | Yes | Yes | Yes |
| Drying 100° C., 16 hours | Yes | Yes | Yes |
| Flake thickness, mm | 0.16 to 0.18 | 0.16 to 0.18 | 0.16 to 0.18 |
| Content of catalyst (vs flake), % | 0.6 | 0.5 | 0.4 |
| Methanol/seed mass ratio | 2 | 2 | 2 |
| Test balance | | | |
| Yield of solids, % (1) | 107.9 | 116.2 | 113.3 |
| Ester/glycerol phase separation | Yes | Yes | Yes |
| Yield of methyl esters, % | 83.7 (3) | 81.7 | 65.9 |
| Ester potential in the cake, % | 2.3 | 1.7 | 2.6 |
| Fat content in the cake, % DM | 1.1 | 0.8 | 1.2 |
| Glycerol yield, % | 469.3 | 453.5 | 574.2 |
| Loss of esters (calculated value), % (2) | 14.0 | 16.6 | 31.5 |

(1) The yield of solids is the ratio times 100 of the solids obtained after evaporation of the miscella to the sum of the theoretical amounts of ester and glycerol
(2) Loss of ester = 100 − ester yield − cake ester potential
(3) Ester not washed since strong emulsion Comments:

the yields of esters produced in the presence of 0.4% and 0.5% of catalyst are, respectively, between 83% and 66%.
the glycerol yields are always very high (>>400%), underlining the presence of other compounds in the glycerol fraction;
under the conditions of tests E29, E30 and E31, the cakes are still slightly charged with fat, with the exception of that obtained in test 10-E31;
in the light of table 5, it turns out that the esters produced are highly charged with glycerides, of the order of 50%.
similarly, the acidity of the esters is very high ($I_A$>5, table 11).
The transesterifying activity is thus still highly insufficient;
the analysis of the fat fraction indicates a lesquerolic acid content of 50% as opposed to 52% in the seed parent oil (table 1).

A test comprising neutralization of the liquid phases was thus performed.

TABLE 11

Analytical balance of the esters

|  | Method | TEST 10-E30 | TEST 10-E31 |
|---|---|---|---|
| Catalyst content (vs flake), % | — | 0.4 | 0.5 |
| Acid number (mg KOH/g) | EN 14104 | 6.1 | 5.1 |
| Monoglyceride content (%) | EN 14105 | 17.2 | 14.2 |
| Diglyceride and triglyceride content (%) |  | 38.1 | 34.6 |

Comments:

TABLE 12

Fatty acid profiles of tests 10-E30 and 10-E3

|  | Method | TEST 10-E30 | TEST 10-E31 |
|---|---|---|---|
| Catalyst content (vs flake), % | — | 0.4 | 0.5 |
| Content of MeC16:0 (%) | FAME | 1.6 | 1.6 |
| Content of MeC16:1 (%) |  | 0.7 | 0.7 |
| Content of MeC18:0 (%) |  | 2.4 | 2.4 |
| Content of MeC18:1 (%) |  | 18.9 | 18.6 |
| Content of RM (%) |  | 0.8 | 0.6 |
| Content of MeC18:2 (%) |  | 10.0 | 10.0 |
| Content of MeC18:2-OH (%) |  | 0.2 | 0.1 |
| Content of MeC18:3 + MeC20:0 (%) |  | 11.8 | 12.3 |
| Content of MeC20:1 (%) |  | 1.1 | 1.1 |
| Content of ML (%)* |  | 50.1 | 50.0 |
| Content of MeC20:2-OH (%) |  | 2.4 | 2.6 |

*ML: Methyl lesquerolate

3—Impact of the Neutralization of the Miscella on the Final Quality of the Esters A neutralization test was thus performed on a sample of miscella from test 10-E31.

The neutralization is performed as follows:

1. The liquids (miscella+washes) are combined in a flask.
2. The amount of sulfuric acid necessary to neutralize is added $m_{H2SO4}=0.2\% \times m_{ES\ non-neutra}$.
3. The methanol is distilled off on a rotary evaporator. Neutralization takes place during the distillation.

TABLE 13

Mass balance of the process for the reactive trituration of *lesquerella* seed with neutralization of the miscella

|  | TEST 10-E31 | TEST 10-E31 Neutra |
|---|---|---|
| Crushing tight flat rollers | Yes | Yes |
| Drying 100° C., 16 hours | Yes | Yes |
| Flake thickness, mm | 0.16 to 0.18 | 0.16 to 0.18 |
| Content of catalyst (vs flake), % | 0.5 | 0.5 |
| Methanol/seed mass ratio | 2 | 2 |
| Neutralization of the miscella | No | Yes |
| Test balance | | |
| Yield of solids, % (1) | 116.2 | 114.7 |
| Ester/glycerol phase separation | Yes | Yes |
| Yield of methyl esters, % | 81.7 | 80.1 |
| Ester potential in the cake, % | 1.7 | 1.7 |
| Fat content in the cake, % DM | 0.8 | 0.8 |
| Glycerol yield, % | 453.5 | 451.5 |
| Loss of esters (calculated value), % (2) | 16.6 | 18.2 |

(1) The yield of solids is the ratio times 100 of the solids obtained after evaporation of the miscella to the sum of the theoretical amounts of ester and glycerol
(2) Loss of ester = 100 − ester yield − cake ester potential Comments:

the neutralization of the miscella is reflected in the following manner:
  no gain in esters,
  no impact on the final glycerol yield, still very high (>>400%),
  no significant impact on the losses of esters "outside cake";
In qualitative terms 1415), it is noted that the neutralization of the miscella has no truly remarkable effect on the percentage of glycerides, which is still very high (45%), and also on the acidity. Similarly, analysis of the fat fraction indicates a lesquerolic acid content of 50% as opposed to 52% in the parent oil (table 9).

TABLE 14

Analytical balance of the esters (effect of neutralization of the miscella)

| | Method | TEST 10-E31 | TEST 10-E31 Neutra |
|---|---|---|---|
| Acid number (mg KOH/g) | EN 14104 | 5.1 | 6.1 |
| Monoglyceride content (%) | EN 14105 | 14.2 | 16.5 |
| Diglyceride and triglyceride content (%) | | 34.6 | 29.1 |

TABLE 15

Fatty acid profiles of test 10-E31 and neutralized test 10-E31

| | Method | TEST 10-E31 | TEST 10-E31 Neutra |
|---|---|---|---|
| Catalyst content (vs flake), % | — | 0.5 | 0.5 |
| Content of MeC16:0 (%) | FAME | 1.6 | 1.5 |
| Content of MeC16:1 (%) | | 0.7 | 0.7 |
| Content of MeC18:0 (%) | | 2.4 | 2.3 |
| Content of MeC18:1 (%) | | 18.6 | 18.3 |
| Content of RM (%) | | 0.6 | 0.7 |
| Content of MeC18:2 (%) | | 10.0 | 9.9 |
| Content of MeC18:2-OH (%) | | 0.1 | 0.1 |
| Content of MeC18:3 + MeC20:0 (%) | | 12.3 | 12.0 |
| Content of MeC20:1 (%) | | 1.1 | 1.1 |
| Content of ML* (%) | | 50.0 | 50.9 |
| Content of MeC20:2-OH (%) | | 2.6 | 2.6 |

*ML: Methyl lesquerolate

Reactive Trituration in the Presence of an Apolar Cosolvent (Hexane)—Examples According to the Invention 1—Influence of the Amount of Catalyst As a reminder, the tests were performed under the following conditions:

1. Flaking of the fresh *lesquerella* seed on a flat roller crusher, in a single crushing operation.
2. The flakes are then dried for 16 hours at 100° C.
3. The flakes are placed in the percolation column.
4. The sodium hydroxide solution in the methanol/hexane mixture (50/50) is then circulated on the bed for 30 minutes at 50° C.
5. The miscella is then withdrawn and the bed of flakes is washed by five successive washes with a methanol/hexane mixture (50/50) at 50° C. (5 minutes per wash).
6. The miscella is then evaporated under vacuum at 90° C. and at 20 mbar for 5 minutes.
7. The ester and the glycerol are separated by centrifugation. The ester yield is calculated on the basis of the mass of ester obtained versus the expected theoretical mass of ester.
8. The ester is then washed until neutral by adding hot water and centrifugation, and is then dried under vacuum at 90° C. and 20 mbar for 5 minutes. The acid number and the composition of this ester are then measured.

TABLE 16

Mass balance of the process for the cosolvent reactive trituration of *lesquerella* seed - effect of the amount of catalyst

| | TEST 10-E45 | TEST 10-E46 | TEST 10-E46Bis | TEST 10-E48 |
|---|---|---|---|---|
| Crushing tight flat rollers | Yes | Yes | Yes | Yes |
| Drying 100° C., 16 hours | Yes | Yes | Yes | Yes |

TABLE 16-continued

Mass balance of the process for the cosolvent reactive trituration of *lesquerella* seed - effect of the amount of catalyst

| | TEST 10-E45 | TEST 10-E46 | TEST 10-E46Bis | TEST 10-E48 |
|---|---|---|---|---|
| Flake thickness, mm | 0.16 to 0.18 | 0.16 to 0.18 | 0.16 to 0.18 | 0.16 to 0.18 |
| Content of catalyst (vs flake), % | 0.6 | 1.0 | 1.0 | 1.1 |
| Solvent/seed mass ratio | 2 | 2 | 2 | 2 |
| Test balance | | | | |
| Yield of solids, % (1) | 102.0 | 106.2 | 104.4 | 108.1 |
| Ester/glycerol phase separation | Yes | Yes | Yes | Yes |
| Yield of methyl esters, % | 98.4 (3) | 74.8 | 82.6 | 83.6 |
| Ester potential in the cake, % | 3.0 | 14.1 | 1.8 | 2.0 |
| Fat content in the cake, % DM | 1.1 | 4.3 (4) | 0.7 | 0.8 |
| Glycerol yield, % | 137.2 | 419.6 | 321.6 | 356.4 |
| Loss of esters (calculated value), % (2) | −1.4 | 11.1 | 15.6 | 14.4 |

(1) The yield of solids is the ratio times 100 of the solids obtained after evaporation of the miscella to the sum of the theoretical amounts of ester and of glycerol
(2) Loss of ester = 100 − ester yield − cake ester potential
(3) Ester difficult to wash since strong emulsion
(4) The hypothesis of the formation of a preferential path in the column during the trituration is envisaged since the cake is very poorly defatted. The test is thus repeated and bears the reference 10-E46Bis.

Comments:

the yields of solids remain higher than 100% with an appreciable improvement at a low catalyst content (0.6%). However, the maximum ester yield of 98% at a low catalyst content (0.6%), which is correlated with a reasonable glycerol yield (137%), should be weighted: specifically, the ester is difficult to wash (emulsions) due to the probable presence of gums. The ester yield of 98% is thus overestimated;

at a higher catalyst content, the ester yields are between 74% and 84% and these esters are more easily purifiable. Under these conditions, the glycerol yields are higher (>300%, charged with gums and/or soaps). Similarly, the ester losses remain high (11-15%, saponification) whereas the cakes are for their part generally well depleted (<1% at the highest catalyst contents);

from a qualitative viewpoint (table 17), with the exception of the esters produced at a low catalyst content, the esters are still slightly acidic ($I_A \approx 1$) but, as a reminder, the initial seed was significantly acidic ($I_A = 4.5$). By comparison with the tests performed in the absence of cosolvent, the glyceride content has greatly reduced (1.6% to 2.2%), but this result is also linked to the high acidity of the seed;

analysis of the fat fraction indicates a lesquerolic acid value close to that of the initial oil for the tests performed with a high catalyst content (table 15).

In conclusion, an evaluation is then performed to see whether neutralization of the miscella does not make it possible to increase the ester yield of a process with cosolvent according to the invention.

TABLE 17

Analytical balance of the esters (impact of the amount of catalyst)

| | Method | TEST 10-E45 | TEST 10-E46 | TEST 10-E46Bis | TEST 10-E48 |
|---|---|---|---|---|---|
| Content of catalyst (vs flake), % | — | 0.6 | 1.0 | 1.0 | 1.1 |
| Acid number (mg KOH/g) | EN 14104 | 2.1 | 0.7 | 0.9 | 0.7 |
| Monoglyceride content (%) | EN 14105 | N.d. (1) | 1.4 | 2.0 | 1.7 |

TABLE 17-continued

Analytical balance of the esters (impact of the amount of catalyst)

| | Method | TEST 10-E45 | TEST 10-E46 | TEST 10-E46Bis | TEST 10-E48 |
|---|---|---|---|---|---|
| Diglyceride and triglyceride content (%) | | N.d. (1) | 0.2 | 0.2 | 0 |

(1) During the washes, a strong emulsion was observed, which suggests that the conversion was not complete and that a large amount of glycerides still remains.

TABLE 18

Fatty acid profiles of tests 10-E45, 10-E46, 10-E46Bis and 10-E48

| | Method | TEST 10-E45 | TEST 10-E46 | TEST 10-E46Bis | TEST 10-E48 |
|---|---|---|---|---|---|
| Content of catalyst (vs flake), % | — | 0.6 | 1.0 | 1.0 | 1.1 |
| Content of MeC16:0 (%) | FAME | 1.9 | 1.9 | 1.8 | 1.9 |
| Content of MeC16:1 (%) | | 0.8 | 0.8 | 0.8 | 0.8 |
| Content of MeC18:0 (%) | | 2.4 | 2.4 | 2.3 | 2.4 |
| Content of MeC18:1 (%) | | 18.8 | 18.7 | 18.9 | 18.9 |
| Content of RM (%) | | 0.6 | 0.7 | 0.6 | 0.9 |
| Content of MeC18:2 (%) | | 10.5 | 10.3 | 10.3 | 10.4 |
| Content of MeC18:2-OH (%) | | 0.2 | 0.1 | 0.3 | 0.2 |
| Content of MeC18:3 + MeC20:0 (%) | | 11.7 | 11.5 | 11.7 | 10.4 |
| Content of MeC20:1 (%) | | 1.0 | 1.0 | 1.0 | 1.1 |
| Content of ML* (%) | | 49.6 | 50.3 | 51.6 | 52.4 |
| Content of MeC20:2-OH (%) | | 2.4 | 2.4 | 2.4 | 2.4 |

*ML: Methyl lesquerolate

2—Impact of Neutralization of the Miscella on the Final Quality of the Esters

A neutralization test was thus performed on a miscella sample of the test.

The neutralization is performed as follows:
1. The liquids (miscella+washes) are combined in a flask.
2. The amount of sulfuric acid necessary to neutralize is added $m_{H2SO4} = 0.2\% \times m_{ES\ non-neutra}$.
3. The methanol is distilled off on a rotary evaporator. Neutralization takes place during the distillation.

TABLE 19

Mass balance of test 10-E48 with and without neutralization of miscella

| | TEST 10-E48 | TEST 10-E48 Neutra |
|---|---|---|
| Crushing tight flat rollers | Yes | Yes |
| Drying 100° C., 16 hours | Yes | Yes |
| Flake thickness, mm | 0.16 to 0.18 | 0.16 to 0.18 |
| Content of catalyst (vs flake), % | 1.1 | 1.1 |
| Solvent/seed mass ratio | 2 | 2 |
| Neutralization of the miscella | No | Yes |
| Test balance | | |
| Yield of solids, % (1) | 108.1 | 105.6 |
| Ester/glycerol phase separation | Yes | Yes |
| Yield of methyl esters, % | 83.6 | 87.7 |
| Ester potential in the cake, % | 2.0 | 2.0 |
| Fat content in the cake, % DM | 0.8 | 0.8 |
| Glycerol yield, % | 356.4 | 287.1 |
| Loss of esters (calculated value), % (2) | 14.4 | 10.3 |

(1) The yield of solids is the ratio times 100 of the solids obtained after evaporation of the miscella to the sum of the theoretical amounts of ester and glycerol
(2) Loss of ester = 100 − ester yield − cake ester potential Comments:

neutralization of the miscella makes it possible to substantially improve the yield of esters (83.6%→87.7%) and also the glycerol, which is less charged with impurities;

the losses of esters "outside cake" are also reduced (14.4%→10.3%);

from a qualitative viewpoint (table 20), the esters have gained in acidity ($I_A$=0.7→1.7) but are less charged with glycerides (0.8%). Finally, the miscella neutralizing treatment does not induce any truly notable modification of the lesquerolic acid content of the final esters (table 18).

TABLE 20

Analytical balance of the esters (miscella neutralization effect)

| | Method | Test 10-E48 | Test 10-E48 Neutra |
|---|---|---|---|
| Acid number (mg KOH/g) | EN 14104 | 0.7 | 1.7 |
| Monoglyceride content (%) | EN 14105 | 1.7 | 0.8 |
| Diglyceride and triglyceride content (%) | | 0.0 | 0.0 |

TABLE 21

Fatty acid profiles of test 10-E48 with and without neutralization

| | Method | Test 10-E48 | Test 10-E48 Neutra |
|---|---|---|---|
| Content of MeC16:0 (%) | FAME | 1.9 | 1.8 |
| Content of MeC16:1 (%) | | 0.8 | 0.7 |
| Content of MeC18:0 (%) | | 2.4 | 2.4 |
| Content of MeC18:1 (%) | | 18.9 | 18.8 |
| Content of RM (%) | | 0.9 | 0.6 |
| Content of MeC18:2 (%) | | 10.4 | 10.1 |
| Content of MeC18:2-OH (%) | | 0.2 | 0.1 |
| Content of MeC18:3 + MeC20:0 (%) | | 10.4 | 11.8 |
| Content of MeC20:1 (%) | | 1.1 | 1.1 |
| Content of ML* (%) | | 52.4 | 52.0 |
| Content of MeC20:2-OH (%) | | 2.4 | 2.3 |

*ML: Methyl lesquerolate

3—Impact of the Amount of Acid Employed During the Miscella Neutralization Step

TABLE 22

Mass balance of test 10-E46Bis (without neutralization) and of tests "10-E57" performed with miscella neutralization

| | TEST 10-E46Bis | TEST 10-E57-1 | TEST 10-E57-2 |
|---|---|---|---|
| Crushing tight flat rollers | Yes | Yes | Yes |
| Drying 100° C., 16 hours | Yes | Yes | Yes |
| Flake thickness, mm | 0.16 to 0.18 | 0.16 to 0.18 | 0.16 to 0.18 |
| Content of catalyst (vs flake), % | 1.0 | 1.0 | 1.0 |
| Solvent/seed mass ratio | 2 | 2 | 2 |
| Neutralization of the miscella | No | Yes | Yes |
| H2SO4, % non-neutralized solids | 0 | 0.25 | 0.50 |
| Test balance | | | |
| Yield of solids, % (1) | 104.4 | 104.7 | 104.2 |
| Ester/glycerol phase separation | Yes | Yes | Yes |
| Yield of methyl esters, % | 82.6 | 86.1 | 88.3 |
| Ester potential in the cake, % | 1.8 | 1.2 | 1.2 |
| Fat content in the cake, % DM | 0.7 | 0.5 | 0.5 |
| Glycerol yield, % | 321.6 | 290.2 | 262.7 |

TABLE 22-continued

Mass balance of test 10-E46Bis (without neutralization) and of tests "10-E57" performed with miscella neutralization

|  | TEST 10-E46Bis | TEST 10-E57-1 | TEST 10-E57-2 |
|---|---|---|---|
| Loss of esters (calculated value), % (2) | 15.6 | 12.7 | 10.5 |

(1) The yield of solids is the ratio times 100 of the solids obtained after evaporation of the miscella to the sum of the theoretical amounts of ester and glycol
(2) Loss of ester = 100 − ester yield − cake ester potential Comments:
when the amount of acid employed in the miscella neutralization step increases, the following effects are observed:
the yield of esters increases until it reaches a value of about 88%
the yield of glycerol decreases until it reaches a value of about 262%
the losses of esters "outside cake" decrease (15.6%→10.5%)

TABLE 23

Analytical balance of the esters (miscella neutralization effect)

|  | Method | TEST 10-E46Bis | TEST 10-E57-1 | TEST 10-E57-2 |
|---|---|---|---|---|
| Neutralization | — | No | Yes | Yes |
| H2SO4, % non-neutralized solids | — | 0 | 0.25 | 0.50 |
| Acid number (mg KOH/g) | EN 14104 | 0.9 | 1.5 | 4.0 |
| Monoglyceride content, (%) | EN 14105 | 2.0 | 1.2 | 1.4 |
| Diglyceride and triglyceride content (%) |  | 0.2 | 0.1 | 0.0 |

Comments:
when the amount of acid employed in the miscella neutralization step increases, the following effects are observed in qualitative terms (tables 23 and 24):
the acidity of the final esters tends to increase ($I_A$=0.9→4.0)
the glyceride content of the esters is improved by the neutralization, but remains unchanged in the $H_2SO_4$ introduction range studied. Neutralization of the miscella has no effect on the lesquerolic acid content of the final esters, which remains close to that of the seed oil (table 24).

TABLE 24

Fatty acid profiles (miscella neutralization effect)

|  | Method | TEST 10-E46Bis | TEST 10-E57-1 | TEST 10-E57-2 |
|---|---|---|---|---|
| Neutralization | — | No | Yes | Yes |
| Content of MeC16:0 (%) | FAME | 1.8 | 1.7 | 1.7 |
| Content of MeC16:1 (%) |  | 0.8 | 0.7 | 0.8 |
| Content of MeC18:0 (%) |  | 2.3 | 2.4 | 2.3 |
| Content of MeC18:1 (%) |  | 18.9 | 18.7 | 18.4 |
| Content of RM (%) |  | 0.6 | 0.4 | 1.0 |
| Content of MeC18:2 (%) |  | 10.3 | 10.1 | 10.0 |
| Content of MeC18:2-OH (%) |  | 0.3 | 0.2 | 0.2 |
| Content of MeC18:3 + MeC20:0 (%) |  | 11.7 | 11.7 | 11.7 |
| Content of MeC20:1 (%) |  | 1.0 | 0.9 | 1.0 |
| Content of ML* (%) |  | 51.6 | 52.4 | 52.3 |
| Content of MeC20:2-OH (%) |  | 2.4 | 2.3 | 2.1 |

*ML: Methyl lesquerolate

Reactive Trituration in the Presence of Ethanol Alone (without Cosolvent)—Comparative Examples 1—Influence of the Amount of Catalyst As a reminder, the procedure is as follows:
1. Flaking of the fresh *lesquerella* seed on a flat roller crusher.
2. The flakes are then dried for 16 hours at 100° C.
3. The flakes are placed in the percolation column.
4. The ethanolic sodium hydroxide solution is then circulated over the bed for 30 minutes at 50° C.
5. The miscella is then withdrawn and the bed of flakes is washed by five successive washes with ethanol at 50° C. (5 minutes per wash).
6. The miscella is then evaporated under vacuum at 90° C. and at 20 mbar for 5 minutes.
7. The ester and the glycerol are separated by centrifugation. The ester yield is calculated on the basis of the mass of ester obtained versus the expected theoretical mass of ester.
8. The ester is then washed until neutral by adding hot water and centrifugation, and is then dried under vacuum at 90° C. and 20 mbar for 5 minutes. The acid number and the composition of this ester are then measured.

TABLE 25

Mass balance of the process for the reactive trituration of *lesquerella* seed in the presence of ethanol - effect of the amount of catalyst

|  | TEST 10-E50 | TEST 10-E55 |
|---|---|---|
| Crushing tight flat rollers | Yes | Yes |
| Drying 100° C., 16 hours | Yes | Yes |
| Flake thickness, mm | 0.16 to 0.18 | 0.16 to 0.18 |
| Content of catalyst (vs flake), % | 1.0 | 0.6 |
| Ethanol/seed mass ratio | 2 | 2 |
| Test balance |  |  |
| Yield of solids, % (1) | 90.6 | 97.7 |
| Ester/glycerol phase separation | No | Yes |
| Yield of esters, % | N.d. | 70.6 |
| Ester potential in the cake, % | 7.6 | 6.0 |
| Fat content in the cake, % DM | 3.3 | 2.5 |
| Glycerol yield, % | N.d. | 384.3 |
| Loss of esters (calculated value), % (2) | 92.4 | 23.4 |

(1) The yield of solids is the ratio times 100 of the solids obtained after evaporation of the miscella to the sum of the theoretical amounts of ester and glycerol
(2) Loss of ester = 100 − ester yield − cake ester potential Comments:
in the presence of ethanol alone, the solids are markedly reduced versus methanol (<<100%). However, gums remain entrained: absence of phase separation (test 10-E50) or even high losses of esters (test 10-E55, >23%)
in the presence of ethanol alone, the yield of esters is about 70% and the cakes are poorly depleted (2.5 to 3.3% residual fat);
from a qualitative viewpoint (tables 26 and 27), in the presence of ethanol alone, the esters obtained are sparingly acidic ($I_A$<<1) but are still charged with glycerides (3%). Moreover, the LA content of these esters is only very sparingly modified (table 27).

TABLE 26

Analytical balance of the esters (effect of the catalyst content)

|  | Method | Test 10-E50 | Test 10-E55 |
|---|---|---|---|
| Content of catalyst (vs flake), % | — | 1.0 | 0.6 |
| Acid number (mg KOH/g) | EN 14104 | N.d. (1) | 0.5 |
| Monoglyceride content (%) | EN 14105 | N.d. (1) | 3.0 |
| Diglyceride and triglyceride content (%) |  | N.d.(1) | 0.0 |

(1) No ester was obtained.

TABLE 27

Fatty acid profiles of tests 10-E50 and 10-E55

|  | Method | Test 10-E50 | Test 10-E55 |
|---|---|---|---|
| Content of catalyst (vs flake), % | — | 1.0 | 0.6 |
| Content of EtC16:0 (%) | FAME | N.d. (1) | 1.9 |
| Content of EtC16:1 (%) |  | N.d. (1) | 0.7 |
| Content of EtC18:0 (%) |  | N.d. (1) | 2.7 |
| Content of EtC18:1 (%) |  | N.d. (1) | 20.3 |
| Content of RE (%) |  | N.d. (1) | 0.6 |
| Content of EtC18:2 (%) |  | N.d. (1) | 10.6 |
| Content of EtC18:2-OH (%) |  | N.d. (1) | 0.1 |
| Content of EtC18:3 + EtC20:0 (%) |  | N.d. (1) | 11.7 |
| Content of EtC20:1 (%) |  | N.d. (1) | 1.0 |
| Content of ML* (%) |  | N.d. (1) | 50.3 |
| Content of EtC20:2-OH (%) |  | N.d. (1) | 2.0 |

(1) No ester was obtained
*ML: Methyl lesquerolate

In conclusion, relative to methanol alone, ethanol alone does not afford any significant improvement of the process.

Conclusion of the Reactive Trituration Tests:

The main conclusions of these tests are the following:

the optimal process requires a flake obtained by a single crushing operation (only one passage in the crusher);

the process leading to the best yield of ester requires an "alcohol-cosolvent" mixture (in this case methanol-hexane) and also a step of neutralization of the miscella with sulfuric acid;

using a seed containing 29% acid oil ($I_A>4$) and under the following conditions (cf. test 10-E48 "neutra"):

content of catalyst (vs flake)=1.1% methanol/hexane volume ratio=1 solvent/flake (predried at 110° C., 16 hours) mass ratio=2 miscella neutralization conditions: 0.2% sulfuric acid vs % solids of the miscella before neutralization.

The ester yield is about 88% with a cake that is relatively well depleted at the end of the process (% fat=0.8) and losses of esters ("outside cake") of about 10%. It is possible at this stage to retreat the glycerol in order to increase the overall ester yield of the process.

From a qualitative viewpoint and despite a seed that is initially strongly acidic, the esters obtained are still sparingly acidic ($I_A$=1.7), low in glycerides (0.8% mono) and enriched in lesquerolic acid content relative to those of the seed oil.

Analysis of the Cakes:

TABLE 1B comparison of the composition of *lesquerella* seed, of the cakes obtained from the reactive and nonreactive trituration processes according to the invention, and of a soybean cake

|  | Materials | | | |
|---|---|---|---|---|
|  | Whole seed | Reactive cake | Nonreactive cake | Soybean 48 cake |
| Test | — | 10E48 | 10E47 | — |
| Residual humidity, % | 7.4 | 1.4 | 1.1 | 12.0 |
| Fat, % crude | 27.1 | 0.8 | 0.9 | 2.0 |
| Mineral ash, % crude | 6.8 | 7.9 | 6.3 | 6.3 |
| Corrected mineral ash*, % crude | 6.8 | 6.3 | 6.3 | 6.3 |
| Cellulose, % crude | 14.2 | 17.6 | 18.1 | 5.3 |
| Starch, % crude | 3.3 | 3.1 | 3.2 | — |
| Proteins, % crude | 31.0 | 32.2 | 31.0 | 45.7 |
| Amino acids, % crude | | | | |
| Lysine*** | 1.4 | 1.4 | 1.5 | 1.3 |
| Methionine*** | 0.3 | 0.4 | 0.4 | 0.6 |
| Methionine + Cystine | 0.8 | 1.0 | 1.0 | 1.2 |
| Tryptophan*** | N.d.** | N.d.** | N.d.** | 0.6 |
| Phenylalanine*** | 0.9 | 1.1 | 1.1 | 2.4 |
| Leucine*** | 1.4 | 1.7 | 1.7 | 3.6 |
| Isoleucine | 0.8 | 0.9 | 0.9 | 2.0 |
| Valine*** | 1.0 | 1.2 | 1.2 | 2.2 |
| Threonine*** | 1.1 | 1.2 | 1.2 | 0.8 |
| Histidine | 0.5 | 0.6 | 0.6 | ? |
| Arginine | 1.5 | 1.8 | 2.1 | ? |
| Tyrosine | N.d.** | N.d.** | N.d.** | 1.7 |
| Isoleucine*** | 0.8 | 0.9 | 0.9 | 2.1 |
| Arginine | 1.8 | 2.1 | 2.1 | ? |
| Glycine | 1.2 | 1.3 | 1.3 | ? |
| Aspartic acid | 1.5 | 1.8 | 2.1 | ? |
| Serine | 1.2 | 1.3 | 1.3 | ? |
| Glutamic acid | 3.1 | 3.7 | 3.8 | ? |
| Proline | 1.5 | 1.6 | 1.7 | ? |
| Alanine | 1.5 | 1.8 | 2.1 | ? |
| Unquantified amino acids**** | 9.1 | 9.8 | 8.0 | — |

*taking into account the sodium provided by the catalyst
**N.d. = not determined
***essential amino acids
****tyrosine, tryptophan It is noted that about 30% of the amino acids are not identified (9.1% relative) via the assay method used. These amino acids might be tryptophan and tyrosine, which are amino acids requiring specific extraction and quantification methods. Given the large proportion of unidentified amino acids, it may be that *lesquerella* moreover contains entirely atypical amino acids.

In table 1B, a comparison is made of a soybean 48 cake (standard commercial product), the *lesquerella* whole seed and also cakes derived from the optimized reactive and unreactive trituration processes according to the invention. The following elements thus emerge:

The dehydrated oil-depleted *lesquerella* cakes derived from the process according to the invention have protein contents of greater than 30%. Thus, the two cakes are more sparingly charged than the values expected after drying and defatting (31-32% as opposed to 48% theoretical). This difference may arise from the presence in the cakes of non-protein nitrogen in significant amount (nitrates or nitrites) or else from a dissolution of the proteins in the miscella. The latter hypothesis appears to be the more probable since *lesquerella* proteins are more soluble in basic medium. Evangelista et al. (2009) (M. P. Hojilla-Evangelista, R. L. Evangelista, Industrial Crops and Products, 29 (2009) 466-472) indeed showed a greater solubility (in water) of *lesquerella* proteins at pH 10 and mention proteolysis at pH values above 10. Given the well known effect of ethanol as an agent for denaturing and dissolving proteins, it may be assumed that there is a protein fraction that is extractible with ethanol (methanol), or even proteins that are partly proteolyzed in the presence of sodium hydroxide.

In point of fact, for *lesquerella*, contrary to a standard process with hexane, the reactive and unreactive trituration process therefore does not induce any protein concentration.

The reactive or unreactive trituration process does not induce any major disruption in the aminogram. However, enrichment of the cakes in a few amino acids (alanine, glutamic acid, methionine+cystine, leucine, phenylalanine, valine, aspartic acid and arginine) is observed;

Compared with a soybean cake, a *lesquerella* cake is less rich in proteins (31% as opposed to 45%). It is also, with regard to the relative concentrations, less rich in essential amino acids, in particular cystine and methionine. *Lesquerella* cake is more concentrated in cellulose and starch;

In addition, the cakes derived from the examples (above) of the processes according to the invention contain less than 1% by weight of antinutritional elements.

The high content of gums in *lesquerella* seed (15%) is demonstrated in the course of the reactive and unreactive trituration tests according to the invention. The process according to the invention confirms the advantage of upgrading these gums, which have properties close to those of xanthan gum and gum Arabic.

Examples of a Step of Methyl Lesquerolate Enrichment by Liquid/Liquid Extraction The object of this step is to concentrate the methyl lesquerolate obtained after a reactive trituration process.

Procedure:

The methyl lesquerolate (ML) enrichment step performed in these tests is similar to that described in patent application WO 2010/084 276 relating to the concentration of methyl ricinoleate. In the following tests, hexane was used as cosolvent (apolar solvent). The polar solvent consisted of hydrated methanol (with a variable water content according to the tests).

1. 5 g ML+30 mL apolar+15 mL polar→Φ heavy 1+Φ light 1
2. Φ light 1+15 mL polar→Φ heavy 2+Φ light 2
3. Φ heavy 1+Φ heavy 2+30 mL apolar→Φ heavy 3+Φ light 3
4. Φ heavy 3+30 mL apolar→Φ heavy 4+Φ light 4

Concentration step:
1. Φ heavy 4→polar fraction
2. Φ light 2+Φ light 3+Φ light 4→apolar fraction Extraction Test No. 1 with 90% Methanol:

TABLE 1C

Analytical balance of the esters obtained from extraction N°1

| | Starting material | Heavy phase Test 1 | Light phase Test 1 |
|---|---|---|---|
| Polar solvent | | 90% methanol | 90% methanol |
| Apolar solvent | | Hexane | Hexane |
| Mass yield, % | | 3.5 | 96.5 |
| ML extraction yield, % | | 3.9 | 95.1 |
| Acid number | 0.72 | N.d. | 0.89 |
| MeC16:1 (%) | 0.5 | 0.1 | 0.5 |
| MeC16 (%) | 1.3 | 0.2 | 1.4 |
| MeC18:2 (%) | 9.1 | 1.1 | 9.6 |
| MeC18:1 (%) | 23.5 | 0.8 | 24.8 |
| Me C18:0 (%) | 1.8 | 0.1 | 1.9 |
| Me C20:0 (%) | 0.9 | 0.1 | 1.0 |

TABLE 1C-continued

Analytical balance of the esters obtained from extraction N°1

| | Starting material | Heavy phase Test 1 | Light phase Test 1 |
|---|---|---|---|
| Me C20:1 (%) | 1.0 | 0.0 | 0.9 |
| MeC18:1-OH (%) | 0.3 | 0.4 | 0.3 |
| MeC20:1-OH (%) | 60.3 | 67.5 | 59.4 |
| Monoglyceride (%) | 1.7 | 29.8 | 0.8 |
| Diglyceride (%) | 0.1 | 0.0 | 0.0 |
| Triglyceride (%) | 0.0 | 0.0 | 0.0 |

Comments

In the course of this liquid-liquid extraction test, the ML extraction yield is about 4%;

In an identical manner to what we already observed with the castor-oil plant, the monoglycerides are greatly concentrated in the methanol phase (>29%) and, in fact, are at a lower content in the light phase than in the starting ester;

In the course of this test, the ML content rises from 60.3% to 67.5% in the polar heavy phase;

An attempt is made to reduce the degree of hydration of the methanol in order to increase the ML extraction yield.

Extraction Test No. 2 with 95% Methanol:

TABLE 2C

Analytical balance of the esters derived from extraction N°2

| | Starting material | Heavy phase Test 2 | Light phase Test 2 |
|---|---|---|---|
| Polar solvent | | 95% methanol | 95% methanol |
| Apolar solvent | | Hexane | Hexane |
| Mass yield, % | | 16.5 | 83.5 |
| ML extraction yield, % | | 25.4 | 74.8 |
| Acid number | 0.72 | N.d. | 1.12 |
| MeC16:1 (%) | 0.5 | 0.1 | 0.6 |
| MeC16 (%) | 1.3 | 0.1 | 1.6 |
| MeC18:2 (%) | 9.1 | 0.6 | 11.7 |
| MeC18:1 (%) | 23.5 | 0.3 | 27.5 |
| Me C18:0 (%) | 1.8 | 0.1 | 2.2 |
| Me C20:0 (%) | 0.9 | 0.0 | 1.1 |
| Me C20:1 (%) | 1.0 | 0.0 | 0.7 |
| MeC18:1-OH (%) | 0.3 | 0.2 | 0.3 |
| MeC20:1-OH (%) | 60.3 | 92.9 | 54.0 |
| Monoglyceride (%) | 1.7 | 5.8 | 0.8 |
| Diglyceride (%) | 0.1 | 0.0 | 0.1 |
| Triglyceride (%) | 0.0 | 0.0 | 0.0 |

Comments

In the course of this liquid-liquid extraction test, the ML extraction yield is markedly increased (4%→>29%) when the degree of hydration of the methanol is reduced by 5 points;

In the course of this test, the ML content rises spectacularly from 60.3% to 92.9% in the polar heavy phase;

for their part, the monoglycerides fall to a content of 5.8% in the methanol phase;

thus, we continued the reduction of the degree of hydration of the methanol in order to further increase the ML extraction yield.

Extraction Test No. 3 with 97% Methanol

In this test, we changed the starting material batch. The ester used is less charged with monoglycerides than the previous ester.

TABLE 3C

Analytical balance of the esters derived from extraction N°3

| | Starting material | Heavy ester Test 3 | Light ester Test 3 |
|---|---|---|---|
| Polar solvent | | 97% methanol | 97% methanol |
| Apolar solvent | | Hexane | Hexane |
| Mass yield, % | | 21.3 | 78.7 |
| ML extraction yield, % | | 33.7 | 66.7 |
| Acid number | 1.68 | N.d. | 1.42 |
| MeC16:1 (%) | 0.5 | 0.0 | 0.6 |
| MeC16 (%) | 1.4 | 0.1 | 1.7 |
| MeC18:2 (%) | 8.1 | 0.7 | 13.4 |
| MeC18:1 (%) | 25.2 | 1.9 | 28.3 |
| Me C18:0 (%) | 1.8 | 0.1 | 2.4 |
| Me C20:0 (%) | 0.9 | 0.0 | 1.2 |
| Me C20:1 (%) | 0.9 | 0.0 | 0.7 |
| MeC18:1-OH (%) | 0.3 | 0.2 | 0.3 |
| MeC20:1-OH (%) | 60.5 | 95.6 | 51.3 |
| Monoglyceride (%) | 0.8 | 1.5 | 0.7 |
| Diglyceride (%) | 0.0 | 0.0 | 0.2 |
| Triglyceride (%) | 0.0 | 0.0 | 0.0 |

Comments

In the course of this liquid-liquid extraction test, the ML extraction yield is again increased (25%→>33%) when the degree of hydration of the methanol is reduced to 3%;

In the course of this test, the ML content rises less spectacularly than in the preceding test (+30 points of ML vs+32% previously);

the monoglyceride content in the extracted ester returns to a reasonable value at 1.5%.

Extraction Test No. 4 with 98% Methanol

TABLE N°4

Analytical balance of the esters derived from extraction N°4

| | Starting material | Heavy ester Test 4 | Light ester Test 4 |
|---|---|---|---|
| Polar solvent | | 98% methanol | 98% methanol |
| Apolar solvent | | Hexane | Hexane |
| Mass yield, % | | 24.4 | 75.6 |
| ML extraction yield, % | | 36.7 | 65.1 |
| Acid number | 1.68 | N.d. | 1.40 |
| MeC16:1 (%) | 0.5 | 0.1 | 0.6 |
| MeC16 (%) | 1.4 | 0.2 | 1.6 |
| MeC18:2 (%) | 8.1 | 1.4 | 14.3 |
| MeC18:1 (%) | 25.2 | 4.0 | 26.6 |
| Me C18:0 (%) | 1.8 | 0.2 | 2.4 |
| Me C20:0 (%) | 0.9 | 1.7 | 0.7 |
| Me C20:1 (%) | 0.9 | 0.1 | 1.2 |
| MeC18:1-OH (%) | 0.3 | 0.2 | 0.3 |
| MeC20:1-OH (%) | 60.5 | 90.9 | 52.1 |
| Monoglyceride (%) | 0.8 | 1.4 | 0.7 |
| Diglyceride (%) | 0.0 | 0.0 | 0.2 |
| Triglyceride (%) | 0.0 | 0.0 | 0.0 |

Comments

In the course of this liquid-liquid extraction test, the ML extraction yield is again increased (>36%) when the degree of hydration of the methanol is down to 2%;

In the course of this test, the ML content in the extracted ester is about 91%, i.e. more than 30 points more than the starting material;

the monoglyceride content in the extracted ester remains stable at 1.4%.

These tests as a whole demonstrate the feasibility of a liquid-liquid extraction process for obtaining an ester concentrated in lesquerolic acid (>90%).

This concentrated ester may optionally be used to produce a synthetic oil enriched in hydroxylated acids.

In the final analysis, the process according to the invention improves both the extractability of the lipids and the esters from *lesquerella* seeds. It in particular succeeds in efficiently concentrating lesquerolic acid.

The invention claimed is:

1. A process for extracting *lesquerella* seeds having a degree of acidity of less than 6 mg KOH/g, said process comprising the following steps:
    a step i) of conditioning the seeds comprising only one crushing operation and at least one seed drying operation;
    a step ii) of placing the conditioned seeds in contact with a mixture of anhydrous light alcohol and of cosolvent under temperature and time conditions that are sufficient to extract a raw oil comprising phospholipids and gums, on the one hand, and to obtain an oil-depleted cake, on the other hand;
    wherein the mixture of step ii) also comprises a basic catalyst under temperature and time conditions that are sufficient to simultaneously extract and trans-esterify the oil and to obtain fatty acid esters and glycerol, on the one hand, and a cake, on the other hand;
    wherein the fatty acid esters and the glycerol are separated by centrifugation; and
    wherein the fatty acid esters are washed until neutral according to the following steps:
        addition of hot water, centrifugation, followed by drying under vacuum at a temperature of between 80° C. and 100° C. and at a pressure within the range from 10 mbar to 30 mbar.

2. The process as claimed in claim 1, in which step ii) is followed by a step iii) of separating the gums from the raw oil to obtain a degummed oil.

3. The process as claimed in claim 2, in which step iii) is followed by a step iv) of separating the phospholipids from the degummed oil by refining the degummed oil.

4. The process as claimed in claim 3, in which the refining of the oil comprises at least one of the following steps:
    demucilagination with phosphoric acid, and/or
    deodorization under vacuum, and/or
    decolorization over decolorizing earths.

5. The process as claimed in claim 1, in which the catalyst/(alcohol-cosolvent)/seeds mass ratio is within the range 0.001 to 0.1/1 to 10/1.

6. The process as claimed in claim 1, in which the basic catalyst is sodium hydroxide.

7. The process as claimed in claim 1, also comprising at least one step of liquid/liquid extraction of said fatty acid esters using light alcohol counter-currentwise relative to the cosolvent, leading to the production of an alcohol phase enriched in lesquerolic acid esters, and of a cosolvent phase containing other fatty acid esters.

8. The process as claimed in claim 1, in which the diameter of the seeds used is less than 1 mm.

9. The process as claimed in claim 1, in which the seeds used in step i) are fresh seeds that have not undergone preheating.

10. The process as claimed in claim 1, in which the crushing operation is performed using a mechanical flat roller crusher.

11. The process as claimed in claim 1, in which the at least one seed drying operation is performed at a temperature of between 80° C. and 120° C.

12. The process as claimed in claim 1, in which the at least one seed drying operation is performed rapidly after the crushing operation, in less than one hour, at a temperature that is sufficient to reduce the moisture content of the seeds to 2% by weight or less.

13. The process as claimed in claim 1, in which the (alcohol-cosolvent)/seeds mass ratio is within the range from 1 to 10.

14. A process for extracting *lesquerella* seeds having a degree of acidity of less than 6 mg KOH/g, said process comprising the following steps:
   a step i) of conditioning the seeds comprising only one crushing operation and at least one seed drying operation;
   a step ii) of placing the conditioned seeds in contact with a mixture of anhydrous light alcohol and of cosolvent under temperature and time conditions that are sufficient to extract a raw oil comprising phospholipids and gums, on the one hand, and to obtain an oil-depleted cake, on the other hand, in which step ii) comprises the following steps:
   percolation in 3 to 9 stages of the mixture counter-currentwise relative to the seeds, at a temperature ranging from 30° C. to 75° C., for 15 minutes to 60 minutes, and then
   separation and recovery of a cake and a liquid miscella,
   removal of the mixture of alcohol and cosolvent from the miscella, by evaporation of said mixture at a temperature of between 80° C. and 100° C. at a pressure in the range from 10 mbar to 30 mbar.

15. The process as claimed in claim 14, in which step ii) also comprises a step of washing the cake with the alcohol/cosolvent mixture, said washing being performed by at least 3 successive washes at a temperature within the range from 30° C. to 50° C.

16. The process as claimed in claim 15, in which step ii) also comprises a step of neutralizing the miscella using a strong acid, such as sulfuric acid, the acid content representing from 0.1% to 1% relative to the solids content of the miscella before neutralization.

17. The process as claimed in claim 1, in which steps i) and ii) are performed continuously.

18. The process as claimed in claim 1, in which the anhydrous light alcohol/cosolvent volume ratio is within the range from 0.5 to 2.

19. The process as claimed in claim 1, in which the anhydrous light alcohol is methanol and the cosolvent is hexane.

20. A crude *lesquerella* oil obtained according to the process of claim 1, wherein it contains at least 50% by weight of lesquerolic acid, at least 0.5% of hydroxylated-chain phospholipids and at least 0.5% of gums.

21. Esters obtained according to the process of claim 1, where a methyl lesquerolate content is greater than 52%.

22. An oil-depleted cake obtained according to the process of claim 1, wherein it comprises:
   less than 3% oil and preferably less than 1% oil,
   at least 20% by weight of cellulose and/or starch, and
   less than 1% by weight of antinutritional elements,
relative to the total weight of the cake.

23. Animal feed comprising the cake as claimed in claim 22.

24. *Lesquerella* gums obtained according to the process of claim 2, wherein the *lesquerella* gums are partially liposoluble and have a degree of acidity of greater than 5 mg KOH/g.

25. *Lesquerella* phospholipids obtained according to the process of claim 2, wherein the *lesquerella* phospholipids comprise at least one hydroxylated chain.

26. An industrial device for performing the process as claimed in claim 1, wherein the device comprises at least:
   a means for conditioning *lesquerella* seeds according to step i), and
   a means for placing the conditioned seeds in contact with a mixture of anhydrous light alcohol and of cosolvent according to step ii), said contact means also comprising a feed of basic catalyst that is circulated or stopped according to the demand, respectively, for lesquerolic ester or *lesquerella* oil.

* * * * *